(12) United States Patent
Yahnker et al.

(10) Patent No.: US 11,591,906 B2
(45) Date of Patent: Feb. 28, 2023

(54) CUTTING TOOL WITH POROUS REGIONS

(71) Applicant: California Institute of Technology, Pasadena, CA (US)

(72) Inventors: Christopher R. Yahnker, Pasadena, CA (US); Mark S. Anderson, Pasadena, CA (US); Douglas C. Hofmann, Pasadena, CA (US); Morgan Hendry, Pasadena, CA (US); Samad A. Firdosy, Pasadena, CA (US); Andre M. Pate, Pasadena, CA (US); Luis Phillipe C.F. Tosi, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 376 days.

(21) Appl. No.: 16/813,391

(22) Filed: Mar. 9, 2020

(65) Prior Publication Data
US 2020/0284146 A1     Sep. 10, 2020

Related U.S. Application Data

(60) Provisional application No. 62/815,254, filed on Mar. 7, 2019.

(51) Int. Cl.
*E21B 49/08* (2006.01)
*G01N 33/24* (2006.01)
(Continued)

(52) U.S. Cl.
CPC .............. *E21B 49/08* (2013.01); *E21B 25/00* (2013.01); *E21B 49/005* (2013.01);
(Continued)

(58) Field of Classification Search
CPC .......... E21B 49/08; E21B 49/00; E21B 25/00; E21B 49/005; E21B 25/02; E21B 21/00;
(Continued)

(56) References Cited

U.S. PATENT DOCUMENTS 2,190,492 A    2/1940 Staples
2,931,249 A    4/1960 Walton
(Continued)

FOREIGN PATENT DOCUMENTS

CN    101709773 A    5/2010
CN    102563006 A    7/2012
(Continued)

OTHER PUBLICATIONS

Kuhn et al., "Microstructure and mechanical properties of slowly cooled Zr—Nb—Cu—Ni—Al composites with ductile bcc phase", Materials Science and Engineering: A, vol. 375-377, Jul. 2004, pp. 322-326.
(Continued)

*Primary Examiner* — Raul J Rios Russo
(74) *Attorney, Agent, or Firm* — KPPB LLP

(57) ABSTRACT

A cutting tool with a cutting region and a connecting support region where the support region is designed to connect to an external motor assembly. The cutting tool is also has a porous region that is integrated within a portion of the tool such that as the tool cuts material the porous region can allow samples of the cut material to permeate into an internal chamber of the tool. Once in the internal chamber material samples can be analyzed in-situ for direct composition analysis.

21 Claims, 14 Drawing Sheets

(51) Int. Cl.
  *G01N 21/3563* (2014.01)
  *E21B 25/00* (2006.01)
  *E21B 49/00* (2006.01)
  *E21B 25/02* (2006.01)
  *E21B 21/00* (2006.01)

(52) U.S. Cl.
  CPC ......... *G01N 21/3563* (2013.01); *G01N 33/24* (2013.01); *E21B 21/00* (2013.01); *E21B 25/02* (2013.01)

(58) Field of Classification Search
  CPC .... G01N 21/3563; G01N 33/24; G01N 21/31; G01N 2021/0314; G01N 2021/0339; B23B 51/02; B33Y 80/00
  See application file for complete search history.

(56) References Cited

U.S. PATENT DOCUMENTS

| | | |
|---|---|---|
| 3,119,283 A | 1/1964 | Itzhak |
| 3,435,512 A | 4/1969 | Macrobbie |
| 3,519,444 A | 7/1970 | Brown et al. |
| 3,529,457 A | 9/1970 | Bowers |
| 3,682,606 A | 8/1972 | Anderson et al. |
| 3,986,412 A | 10/1976 | Farley et al. |
| 4,123,737 A | 10/1978 | Hoagland, Jr. |
| RE29,989 E | 5/1979 | Polk et al. |
| 4,173,393 A | 11/1979 | Maurer |
| 4,202,404 A | 5/1980 | Carlson |
| 4,662,259 A | 5/1987 | Dutina |
| 4,670,636 A | 6/1987 | Taub et al. |
| 4,711,795 A | 12/1987 | Takeuchi et al. |
| 4,749,625 A | 6/1988 | Obayashi et al. |
| 4,783,983 A | 11/1988 | Narasimhan |
| 4,810,314 A | 3/1989 | Henderson et al. |
| 4,812,150 A | 3/1989 | Scott |
| 4,823,638 A | 4/1989 | Ishikawa |
| 4,851,296 A | 7/1989 | Tenhover et al. |
| 4,883,632 A | 11/1989 | Goto et al. |
| 4,935,291 A | 6/1990 | Gunnink |
| 5,168,918 A | 12/1992 | Okuda et al. |
| 5,185,198 A | 2/1993 | Lefeber et al. |
| 5,288,344 A | 2/1994 | Peker et al. |
| 5,310,432 A | 5/1994 | Yamanaka et al. |
| 5,485,761 A | 1/1996 | Rouverol |
| 5,509,978 A | 4/1996 | Masumoto et al. |
| 5,636,550 A | 6/1997 | Deane |
| 5,722,295 A | 3/1998 | Sakai et al. |
| 5,746,844 A | 5/1998 | Sterett et al. |
| 5,772,803 A | 6/1998 | Peker et al. |
| 5,866,272 A | 2/1999 | Westre et al. |
| 5,896,642 A | 4/1999 | Peker et al. |
| 5,985,204 A | 11/1999 | Otsuka et al. |
| 6,162,130 A | 12/2000 | Masumoto et al. |
| 6,273,322 B1 | 8/2001 | Yamamoto et al. |
| 6,321,738 B1 | 11/2001 | Walsh |
| 6,620,264 B2 | 9/2003 | Kundig et al. |
| 6,652,679 B1 | 11/2003 | Inoue et al. |
| 6,771,490 B2 | 8/2004 | Peker et al. |
| 6,843,496 B2 | 1/2005 | Peker et al. |
| 6,887,586 B2 | 5/2005 | Peker et al. |
| 7,052,561 B2 | 5/2006 | Lu et al. |
| 7,073,560 B2 | 7/2006 | Kang et al. |
| 7,075,209 B2 | 7/2006 | Howell et al. |
| 7,323,071 B1 | 1/2008 | Branagan |
| 7,357,731 B2 | 4/2008 | Johnson et al. |
| 7,360,419 B2 | 4/2008 | French et al. |
| 7,497,981 B2 | 3/2009 | Graham et al. |
| 7,500,987 B2 | 3/2009 | Bassler et al. |
| 7,540,929 B2 | 6/2009 | Demetriou et al. |
| 7,552,664 B2 | 6/2009 | Bulatowicz |
| 7,575,040 B2 | 8/2009 | Johnson |
| 7,862,323 B2 | 1/2011 | Micarelli et al. |
| 7,883,592 B2 | 2/2011 | Hofmann et al. |
| 7,896,982 B2 | 3/2011 | Johnson et al. |
| 7,955,713 B2 | 6/2011 | Roebroeks et al. |
| 8,042,770 B2 | 10/2011 | Martin et al. |
| 8,400,721 B2 | 3/2013 | Bertele et al. |
| 8,418,366 B2 | 4/2013 | Wang et al. |
| 8,485,245 B1 | 7/2013 | Prest et al. |
| 8,496,077 B2 | 7/2013 | Nesnas et al. |
| 8,596,106 B2 | 12/2013 | Tang et al. |
| 8,613,815 B2 | 12/2013 | Johnson et al. |
| 8,639,484 B2 | 1/2014 | Wei et al. |
| 8,789,629 B2 | 7/2014 | Parness et al. |
| 8,986,469 B2 | 3/2015 | Khalifa et al. |
| 9,044,805 B2 | 6/2015 | Prest et al. |
| 9,057,120 B2 | 6/2015 | Pham et al. |
| 9,211,564 B2 | 12/2015 | Hofmann |
| 9,328,813 B2 | 5/2016 | Hofmann et al. |
| 9,579,718 B2 | 2/2017 | Hofmann |
| 9,610,650 B2 | 4/2017 | Hofmann et al. |
| 9,783,877 B2 | 10/2017 | Hofmann et al. |
| 9,791,032 B2 | 10/2017 | Hofmann et al. |
| 9,868,150 B2 | 1/2018 | Hofmann et al. |
| 9,996,053 B2 | 6/2018 | O'keeffe et al. |
| 10,081,136 B2 | 9/2018 | Hofmann et al. |
| 10,151,377 B2 | 12/2018 | Hofmann et al. |
| 10,155,412 B2 | 12/2018 | Parness et al. |
| 10,174,780 B2 | 1/2019 | Hofmann et al. |
| 10,471,652 B2 | 11/2019 | Hofmann et al. |
| 10,487,934 B2 | 11/2019 | Kennett et al. |
| 10,690,227 B2 | 6/2020 | Hofmann et al. |
| 11,400,613 B2 | 8/2022 | Hofmann et al. |
| 2002/0053375 A1 | 5/2002 | Hays et al. |
| 2002/0100573 A1 | 8/2002 | Inoue et al. |
| 2002/0184766 A1 | 12/2002 | Kobayashi et al. |
| 2003/0052105 A1 | 3/2003 | Nagano et al. |
| 2003/0062811 A1 | 4/2003 | Peker et al. |
| 2003/0209125 A1 | 11/2003 | Bertolet |
| 2004/0035502 A1 | 2/2004 | Kang et al. |
| 2004/0103536 A1 | 6/2004 | Kobayashi et al. |
| 2004/0103537 A1 | 6/2004 | Kobayashi et al. |
| 2004/0154701 A1 | 8/2004 | Lu et al. |
| 2005/0034792 A1 | 2/2005 | Lu et al. |
| 2005/0084407 A1 | 4/2005 | Myrick |
| 2005/0127139 A1 | 6/2005 | Slattery et al. |
| 2005/0172777 A1 | 8/2005 | Olander et al. |
| 2005/0263932 A1 | 12/2005 | Heugel |
| 2006/0105011 A1 | 5/2006 | Sun et al. |
| 2006/0130944 A1 | 6/2006 | Poon et al. |
| 2006/0156785 A1 | 7/2006 | Mankame et al. |
| 2007/0034304 A1 | 2/2007 | Inoue et al. |
| 2007/0144621 A1 | 6/2007 | Farmer et al. |
| 2007/0226979 A1 | 10/2007 | Paton et al. |
| 2007/0228592 A1 | 10/2007 | Dunn et al. |
| 2007/0253856 A1 | 11/2007 | Vecchio et al. |
| 2007/0266841 A1 | 11/2007 | Robinson et al. |
| 2008/0085368 A1 | 4/2008 | Gauthier et al. |
| 2008/0099175 A1 | 5/2008 | Chu et al. |
| 2008/0121316 A1 | 5/2008 | Duan et al. |
| 2008/0190521 A1 | 8/2008 | Loffler et al. |
| 2008/0304975 A1 | 12/2008 | Clark et al. |
| 2009/0011846 A1 | 1/2009 | Scott |
| 2009/0078370 A1 | 3/2009 | Sklyarevich et al. |
| 2009/0114317 A1 | 5/2009 | Collier et al. |
| 2009/0194205 A1 | 8/2009 | Loffler et al. |
| 2009/0246398 A1 | 10/2009 | Kurahashi et al. |
| 2009/0263582 A1 | 10/2009 | Batchelder |
| 2009/0277540 A1 | 11/2009 | Langlet |
| 2009/0288741 A1 | 11/2009 | Zhang et al. |
| 2010/0313704 A1 | 12/2010 | Wang et al. |
| 2011/0048587 A1 | 3/2011 | Vecchio et al. |
| 2011/0154928 A1 | 6/2011 | Ishikawa |
| 2011/0302783 A1 | 12/2011 | Nagata et al. |
| 2012/0006085 A1 | 1/2012 | Johnson et al. |
| 2012/0067100 A1 | 3/2012 | Stefansson et al. |
| 2012/0073710 A1 | 3/2012 | Kim et al. |
| 2012/0077052 A1 | 3/2012 | Demetriou et al. |
| 2012/0132631 A1 | 5/2012 | Wescott et al. |
| 2012/0133080 A1 | 5/2012 | Moussa et al. |
| 2012/0289946 A1 | 11/2012 | Steger |
| 2013/0009338 A1 | 1/2013 | Mayer |

(56) References Cited

U.S. PATENT DOCUMENTS

| | | |
|---|---|---|
| 2013/0039708 A1 | 2/2013 | Stenman |
| 2013/0048152 A1 | 2/2013 | Na et al. |
| 2013/0062134 A1 | 3/2013 | Parness et al. |
| 2013/0068527 A1 | 3/2013 | Parness et al. |
| 2013/0112321 A1 | 5/2013 | Poole et al. |
| 2013/0133787 A1 | 5/2013 | Kim |
| 2013/0139964 A1 | 6/2013 | Hofmann et al. |
| 2013/0143060 A1 | 6/2013 | Jacobsen et al. |
| 2013/0255837 A1 | 10/2013 | Peker et al. |
| 2013/0277891 A1 | 10/2013 | Teulet |
| 2013/0280547 A1 | 10/2013 | Brandl et al. |
| 2013/0309121 A1 | 11/2013 | Prest et al. |
| 2013/0316867 A1 | 11/2013 | Kobayashi |
| 2013/0316868 A1 | 11/2013 | Kobayashi |
| 2013/0333814 A1 | 12/2013 | Fleury et al. |
| 2014/0004352 A1 | 1/2014 | McCrea et al. |
| 2014/0010968 A1 | 1/2014 | Prest et al. |
| 2014/0020794 A1 | 1/2014 | Hofmann et al. |
| 2014/0030948 A1 | 1/2014 | Kim et al. |
| 2014/0045680 A1 | 2/2014 | Nakayama et al. |
| 2014/0048969 A1 | 2/2014 | Swanson et al. |
| 2014/0070445 A1 | 3/2014 | Mayer |
| 2014/0083640 A1 | 3/2014 | Waniuk et al. |
| 2014/0090752 A1 | 4/2014 | Waniuk et al. |
| 2014/0093674 A1 | 4/2014 | Hofmann et al. |
| 2014/0130158 A1* | 5/2014 | Wang .................. G06F 21/566 726/23 |
| 2014/0141164 A1 | 5/2014 | Hofmann |
| 2014/0163717 A1 | 6/2014 | Das et al. |
| 2014/0202595 A1 | 7/2014 | Hofmann |
| 2014/0203622 A1 | 7/2014 | Yamamoto et al. |
| 2014/0213384 A1 | 7/2014 | Johnson et al. |
| 2014/0224050 A1 | 8/2014 | Hofmann et al. |
| 2014/0227125 A1 | 8/2014 | Hofmann |
| 2014/0246809 A1 | 9/2014 | Hofmann |
| 2014/0293384 A1 | 10/2014 | O'Keeffe et al. |
| 2014/0312098 A1 | 10/2014 | Hofmann et al. |
| 2014/0332120 A1 | 11/2014 | Liu et al. |
| 2014/0334106 A1 | 11/2014 | Prest et al. |
| 2014/0342179 A1 | 11/2014 | Hofmann et al. |
| 2014/0348571 A1 | 11/2014 | Prest et al. |
| 2015/0014885 A1 | 1/2015 | Hofmann et al. |
| 2015/0044084 A1 | 2/2015 | Hofmann et al. |
| 2015/0047463 A1 | 2/2015 | Hofmann et al. |
| 2015/0068648 A1 | 3/2015 | Schroers et al. |
| 2015/0075744 A1 | 3/2015 | Hofmann et al. |
| 2015/0158067 A1 | 6/2015 | Kumar et al. |
| 2015/0165693 A1 | 6/2015 | Sagoo et al. |
| 2015/0209094 A1 | 7/2015 | Anderson |
| 2015/0209889 A1 | 7/2015 | Peters et al. |
| 2015/0219572 A1 | 8/2015 | Beuth, Jr. et al. |
| 2015/0289605 A1 | 10/2015 | Prest et al. |
| 2015/0298443 A1 | 10/2015 | Hundley et al. |
| 2015/0299825 A1 | 10/2015 | Poole et al. |
| 2015/0314566 A1 | 11/2015 | Mattlin et al. |
| 2015/0323053 A1 | 11/2015 | El-Wardany et al. |
| 2015/0352794 A1 | 12/2015 | Nguyen et al. |
| 2016/0023438 A1 | 1/2016 | Johnson et al. |
| 2016/0175929 A1 | 6/2016 | Colin et al. |
| 2016/0178047 A1 | 6/2016 | Kennett et al. |
| 2016/0186850 A1 | 6/2016 | Hofmann et al. |
| 2016/0233089 A1 | 8/2016 | Zenou et al. |
| 2016/0242877 A1 | 8/2016 | Bernhard |
| 2016/0258522 A1 | 9/2016 | Hofmann et al. |
| 2016/0263937 A1 | 9/2016 | Parness et al. |
| 2016/0265576 A1 | 9/2016 | Hofmann et al. |
| 2016/0299183 A1 | 11/2016 | Lee |
| 2016/0327683 A1* | 11/2016 | Donzier ............... E21B 49/082 |
| 2016/0361765 A1 | 12/2016 | Danger et al. |
| 2016/0361897 A1 | 12/2016 | Hofmann et al. |
| 2017/0021417 A1 | 1/2017 | Martin et al. |
| 2017/0050241 A1 | 2/2017 | Thomas et al. |
| 2017/0121799 A1 | 5/2017 | Hofmann et al. |
| 2017/0137955 A1 | 5/2017 | Hofmann et al. |
| 2017/0144225 A1 | 5/2017 | Hofmann |
| 2017/0211168 A1 | 7/2017 | Liu et al. |
| 2017/0226619 A1 | 8/2017 | Hofmann et al. |
| 2017/0276225 A1 | 9/2017 | Takehana et al. |
| 2017/0305003 A1 | 10/2017 | Tannhaeuser |
| 2017/0321790 A1 | 11/2017 | Klassen et al. |
| 2018/0028088 A1* | 2/2018 | Garbey ............... A61B 5/7405 |
| 2018/0073355 A1* | 3/2018 | Bhongale ............. G01J 3/0218 |
| 2018/0119259 A1 | 5/2018 | Hofmann et al. |
| 2018/0257141 A1 | 9/2018 | Hofmann et al. |
| 2018/0272432 A1 | 9/2018 | Jonsson et al. |
| 2018/0339338 A1 | 11/2018 | Hofmann et al. |
| 2018/0339342 A1 | 11/2018 | Hofmann |
| 2018/0345366 A1 | 12/2018 | Hofmann |
| 2019/0009464 A1 | 1/2019 | Steege |
| 2019/0022923 A1 | 1/2019 | Hofmann et al. |
| 2019/0126674 A1 | 5/2019 | Parness et al. |
| 2019/0154130 A1 | 5/2019 | Hofmann et al. |
| 2019/0170235 A1 | 6/2019 | Hofmann et al. |
| 2019/0177826 A1 | 6/2019 | Hofmann et al. |
| 2019/0195269 A1 | 6/2019 | Hofmann et al. |
| 2019/0255635 A1 | 8/2019 | Hanni et al. |
| 2019/0285608 A1* | 9/2019 | Laird ................. G01N 21/3563 |
| 2019/0314903 A1 | 10/2019 | Haenle et al. |
| 2020/0000595 A1 | 1/2020 | Jones et al. |
| 2020/0056578 A1* | 2/2020 | Sheldon-Coulson ........................ H02K 7/1823 |
| 2020/0278016 A1 | 9/2020 | Hofmann et al. |
| 2020/0278017 A1 | 9/2020 | Hofmann et al. |
| 2020/0282582 A1 | 9/2020 | Hofmann et al. |
| 2020/0318721 A1 | 10/2020 | Hofmann et al. |

FOREIGN PATENT DOCUMENTS

| | | |
|---|---|---|
| CN | 103153502 A | 6/2013 |
| CN | 203227820 U | 10/2013 |
| DE | 102005014972 A1 | 10/2006 |
| DE | 102010062089 A1 | 5/2012 |
| DE | 112018001284 T5 | 11/2019 |
| EP | 0127366 A1 | 5/1984 |
| EP | 1063312 A1 | 12/2000 |
| EP | 1138798 A1 | 10/2001 |
| EP | 1696153 A1 | 8/2006 |
| EP | 1404884 B1 | 7/2007 |
| EP | 1944138 A2 | 7/2008 |
| EP | 3630392 A1 | 4/2020 |
| EP | 3630395 A1 | 4/2020 |
| EP | 3630397 A2 | 4/2020 |
| JP | 61276762 A | 12/1986 |
| JP | 09121094 A | 5/1997 |
| JP | 2002045960 A | 2/2002 |
| JP | 2004315340 A | 11/2004 |
| JP | 2004353053 A | 12/2004 |
| JP | 2007040517 A | 2/2007 |
| JP | 2007040518 A | 2/2007 |
| JP | 2007247037 A | 9/2007 |
| JP | 2008115932 A | 5/2008 |
| JP | 2008264865 A | 11/2008 |
| JP | 2011045931 A | 3/2011 |
| JP | 2012046826 A | 3/2012 |
| JP | 2012162805 A | 8/2012 |
| JP | 2013057397 A | 3/2013 |
| JP | 5249932 B2 | 7/2013 |
| JP | 2013238278 A | 11/2013 |
| JP | 2013544648 A | 12/2013 |
| JP | 2018149655 A | 9/2018 |
| KR | 101420176 B1 | 7/2014 |
| KR | 1020190119154 A | 10/2019 |
| KR | 1020200004435 A | 1/2020 |
| KR | 1020200011470 A | 2/2020 |
| WO | 2006073428 A2 | 7/2006 |
| WO | 2007038882 A1 | 4/2007 |
| WO | 2008058896 A1 | 5/2008 |
| WO | 2008156889 A2 | 12/2008 |
| WO | 2009069716 A1 | 6/2009 |
| WO | 2010027317 A1 | 3/2010 |
| WO | 2011159596 A1 | 12/2011 |
| WO | 2012031022 A2 | 3/2012 |
| WO | 2012083922 A1 | 6/2012 |
| WO | 2012147559 A1 | 11/2012 |

(56) References Cited

FOREIGN PATENT DOCUMENTS

| WO | 2013138710 A1 | 9/2013 |
|---|---|---|
| WO | 2013141878 A1 | 9/2013 |
| WO | 2013141882 A1 | 9/2013 |
| WO | 2014004704 A1 | 1/2014 |
| WO | 2014012113 A2 | 1/2014 |
| WO | 2014058498 A3 | 4/2014 |
| WO | 2015042437 A1 | 3/2015 |
| WO | 2015156797 A1 | 10/2015 |
| WO | 2016116562 A1 | 7/2016 |
| WO | 2018165662 A1 | 9/2018 |
| WO | 2018218077 A1 | 11/2018 |
| WO | 2018218247 A1 | 11/2018 |
| WO | 2018223117 A2 | 12/2018 |
| WO | 2018223117 A3 | 1/2019 |

OTHER PUBLICATIONS

Kuhn et al., "ZrNbCuNiAl bulk metallic glass matrix composites containing dendritic bcc phase precipitates", Applied Physics Letters, vol. 80, No. 14, Apr. 8, 2002, pp. 2478-2480.
Kumar et al., "Bulk Metallic Glass: The Smaller the Better", Advanced Materials, vol. 23, No. 4, 2011, pp. 461-476.
Kwon et al., "Wear behavior of Fe-based bulk metallic glass composites", Journal of Alloys and Compounds, vol. 509S, Jun. 2011, pp. S105-S108.
Launey et al., "Fracture toughness and crack-resistance curve behavior in metallic glass-matrix composites", Applied Physics Letters, vol. 94, Jun. 18, 2009, pp. 241910-1-241910-3.
Launey et al., "Solution to the problem of the poor cyclic fatigue resistance of bulk metallic glasses", PNAS Early Edition, Mar. 31, 2009, pp. 1-6.
Lee et al., "Effect of a controlled volume fraction of dendritic phases on tensile and compressive ductility in La-based metallic glass matrix composites", Acta Materialia, vol. 52, No. 14, Aug. 2004, pp. 4121-4131.
Lee et al., "Nanomechanical properties of embedded dendrite phase and its influence on inelastic deformation of Zr55Al10Ni5Cu30 glassy alloy", Materials Science and Engineering A, vol. 449-451, Mar. 25, 2007, pp. 945-948.
Li et al., "Selective laser melting of Zr-based bulk metallic glasses: Processing, microstructure and mechanical properties", Materials and Design, vol. 112, Sep. 21, 2016, pp. 217-226.
Li et al., "Wear behavior of bulk Zr41Ti14Cu12.5Ni10Be22.5 metallic glasses", Journal of Materials Research, vol. 17, No. 8, Aug. 2002, pp. 1877-1880.
Lillo et al., "Microstructure, Processing, Performance Relationships for High Temperature Coatings", U.S. Department of Energy, Office of Fossil Energy, under DOE Idaho Operations Office, Contract DE-AC07-05ID14517, 22nd Annual Conference on Fossil Energy Materials, Pittsburgh, U.S., Jul. 2008, 8 pgs.
Lin et al., "Designing a toxic-element-free Ti-based amorphous alloy with remarkable supercooled liquid region for biomedical application", Intermetallics, vol. 55, Dec. 2014, pp. 22-27.
List et al., "Impact Conditions for Cold Spraying of Hard Metallic Glasses", Journal of Thermal Spray Technology, vol. 21, No. 3-4, Jun. 2012, pp. 531-540.
Liu et al., "Influence of Heat Treatment on Microstructure and Sliding Wear of Thermally Sprayed Fe-Based Metallic Glass coatings", Tribology Letters, vol. 46, Mar. 4, 2012, pp. 131-138.
Liu et al., "Metallic glass coating on metals plate by adjusted explosive welding technique", Applied Surface Science, vol. 255, No. 23, Sep. 15, 2009, pp. 9343-9347.
Liu et al., "Microstructure and properties of Fe-based amorphous metallic coating produced by high velocity axial plasma spraying", Journal of Alloys and Compounds, vol. 484, No. 1-2, Sep. 18, 2009, pp. 300-307.
Liu et al., "Sliding Tribological Characteristics of a Zr-based Bulk Metallic Glass Near the Glass Transition Temperature", Tribology Letters, vol. 33, 2009, pp. 205-210.
Liu et al., "Wear behavior of a Zr-based bulk metallic glass and its composites", Journal of Alloys and Compounds, vol. 503, No. 1, Jul. 30, 2010, pp. 138-144.
Lupoi et al., "Deposition of metallic coatings on polymer surfaces using cold spray", Surface & Coatings Technology, vol. 205, No. 7, Dec. 25, 2010, pp. 2167-2173.
Ma et al., "Wear resistance of Zr-based bulk metallic glass applied in bearing rollers", Materials Science and Engineering A, vol. 386, No. 1-2, Nov. 25, 2004, pp. 326-330.
Maddala et al., "Effect of notch toughness and hardness on sliding wear of Cu50Hf41.5Al8.5 bulk metallic glass", Scripta Materialia, vol. 65, No. 7, Oct. 2011, pp. 630-633.
Madge, "Toughness of Bulk Metallic Glasses", Metals, vol. 5, pp. Jul. 17, 2015, 1279-1305.
Mahbooba et al., "Additive manufacturing of an iron-based bulk metallic glass larger than the critical casting thickness", Applied Materials Today, vol. 11, Jun. 2018, pp. 264-269.
Narayan et al., "On the hardness and elastic modulus of bulk metallic glass matrix composites", Scripta Materialia, vol. 63, No. 7, Oct. 2010, pp. 768-771.
Ni et al., "High performance amorphous steel coating prepared by HVOF thermal spraying", Journal of Alloys and Compounds, vol. 467, No. 1-2, Jan. 7, 2009, pp. 163-167.
Nishiyama et al., "Recent progress of bulk metallic glasses for strain-sensing devices", Materials Science and Engineering A, vol. 449-451, Mar. 25, 2007, pp. 79-83.
Oh et al., "Microstructure and tensile properties of high-strength high-ductility Ti-based amorphous matrix composites containing ductile dendrites", Acta Materialia, vol. 59, No. 19, Nov. 2011, pp. 7277-7286.
Parlar et al., "Sliding tribological characteristics of Zr-based bulk metallic glass", Intermetallics, vol. 16, No. 1, Jan. 2008, pp. 34-41.
Pauly et al., "Modeling deformation behavior of Cu—Zr—Al bulk metallic glass matrix composites", Applied Physics Letters, vol. 95, No. 10, 2009, pp. 101906-1-101906-3.
Pauly et al., "Processing Metallic Glasses by Selective Laser Melting", Materials Today, vol. 16, Jan./Feb. 2013, pp. 37-41.
Pauly et al., "Transformation-mediated ductility in CuZr-based bulk metallic glasses", Nature Materials, vol. 9, No. 6, May 16, 2010, 5 pgs.
Ponnambalam et al., "Fe-based bulk metallic glasses with diameter thickness larger than one centimeter", Journal of Materials Research, vol. 19, No. 5, May 2004, pp. 1320-1323.
Porter et al., "Incorporation of Amorphous Metals into MEMS for High Performance and Reliability", Rockwell Scientific Company, Final Report, Nov. 2003, 40 pgs.
Prakash et al., "Sliding wear behaviour of some Fe-, Co-and Ni-based metallic glasses during rubbing against bearing steel", Tribology Letters, vol. 8, Mar. 2000, pp. 153-160.
Qiao et al., "Development of plastic Ti-based bulk-metallic-glass-matrix composites by controlling the microstructures", Materials Science and Engineering A, vol. 527, No. 29-30, Nov. 15, 2010, pp. 7752-7756.
Ramamurty et al., "Hardness and plastic deformation in a bulk metallic glass", Acta Materialia, vol. 53, No. 3, Feb. 2005, pp. 705-717.
Revesz et al., "Microstructure and morphology of Cu—Zr—Ti coatings produced by thermal spray and treated by surface mechanical attrition", Journal of Alloys and Compounds, vol. 509S, Jun. 2011, pp. S482-S485.
Rigney et al., "The Evolution of Tribomaterial During Sliding: A Brief Introduction", Tribology Letters, vol. 39, Jul. 2010, pp. 3-7.
Roberts et al., "Cryogenic Charpy impact testing of metallic glass matrix composites", Scripta Materialia, vol. 66, No. 5, Nov. 11, 2011, 4 pgs.
Sanders et al., "Stability of Al-rich glasses in the Al—La—Ni system", Intermetallics, vol. 14, No. 3, Mar. 2006, pp. 348-351.
Schuh et al., "A survey of instrumented indentation studies on metallic glasses", Journal of Materials Research, vol. 19, No. 1, Jan. 2004, pp. 46-57.
Segu et al., "Dry Sliding Tribological Properties of Fe-Based Bulk Metallic Glass", Tribology Letters, vol. 47, Apr. 28, 2012, pp. 131-138.

(56) References Cited

OTHER PUBLICATIONS

Shen et al., "3D printing of large, complex metallic glass structures", Materials and Design, vol. 117, Mar. 2017, pp. 213-222.
Shen et al., "Exceptionally high glass-forming ability of an FeCoCrMoCBY alloy", Applied Physics, vol. 86, No. 15, 2005, pp. 151907-1-151907-3.
Singer et al., "Wear behavior of triode-sputtered MoS2 coatings in dry sliding contact with steel and ceramics", Wear, vol. 195, No. 1-2, Jul. 1996, pp. 7-20.
Sinmazcelik et al., "A review: Fibre metal laminates, background, bonding types and applied test methods", Materials and Design, vol. 32, No. 7, Aug. 2011, pp. 3671-3685.
Song et al., "Strategy for pinpointing the formation of B2 CuZr in metastable CuZr-based shape memory alloys", Acta Materialia, vol. 59, No. 17, Oct. 2011, pp. 6620-6630.
Sun et al., "Fiber metallic glass laminates", Journal of Materials Research, vol. 25, No. 12, Dec. 2010, pp. 2287-2291.
Sundaram et al., "Mesoscale Folding, Instability, and Disruption of Laminar Flow in Metal Surfaces", Physical Review Letters, vol. 109, Sep. 7, 2012, pp. 106001-1-106001-5.
Szuecs et al., "Mechanical Properties of Zr56.2Ti13.8Nb5.0Cu6.9Ni5.6Be12.5 Ductile Phase Reinforced Bulk Metallic Glass Composite", Acta Materialia, vol. 49, No. 9, May 25, 2001, pp. 1507-1513.
Tam et al., "Abrasion resistance of Cu based bulk metallic glasses", Journal of Non-Crystalline Solids, vol. 347, No. 1-3, Nov. 2004, pp. 268-272.
Tam et al., "Abrasive wear of Cu60Zr30Ti10 bulk metallic glass", Materials Science and Engineering A, vol. 384, No. 1-2, Oct. 2004, pp. 138-142.
Tan et al., "Synthesis of La-based in-situ bulk metallic glass matrix composite", Intermetallics, Nov. 2002, vol. 10, No. 11-12, Nov. 2002, pp. 1203-1205.
Extended European Search Report for European Application No. 14889035.3, Search completed Dec. 4, 2017, dated Dec. 13, 2017, 10 Pgs.
International Preliminary Report on Patentability for International Application PCT/US2018/035813, Report dated Dec. 3, 2019, Mailed Dec. 12, 2019, 9 Pgs.
International Preliminary Report on Patentability for International Application PCT/US2013/047950, dated Dec. 31, 2014, Mailed Jan. 8, 2015, 7 Pgs.
International Preliminary Report on Patentability for International Application PCT/US2013/050614, dated Jan. 20, 2015, Mailed Jan. 29, 2015, 9 Pgs.
International Preliminary Report on Patentability for International Application PCT/US2014/033510, dated Oct. 12, 2016, Mailed Oct. 20, 2016, 9 Pgs.
International Preliminary Report on Patentability for International Application PCT/US2014/056615, dated Mar. 22, 2016, Mailed Mar. 31, 2016, 11 Pgs.
International Preliminary Report on Patentability for International Application PCT/US2018/022020, Report dated Sep. 10, 2019, Mailed Sep. 19, 2019, 10 Pgs.
International Preliminary Report on Patentability for International Application PCT/US2018/034481, Report dated Nov. 26, 2019, Mailed Dec. 5, 2019, 17 Pgs.
International Preliminary Report on Patentability for International Application PCT/US2018/034924, Report dated Nov. 26, 2019, Mailed Dec. 5, 2019, 13 Pgs.
International Search Report and Written Opinion for International Application No. PCT/US2013/050614, dated May 7, 2014, Mailed May 7, 2014, 12 pgs.
International Search Report and Written Opinion for International Application No. PCT/US2018/022020, Search completed Jul. 2, 2018, dated Jul. 3, 2018, 12 Pgs.
International Search Report and Written Opinion for International Application No. PCT/US2018/034481, Search completed Sep. 10, 2018, dated Sep. 10, 2018, 19 Pgs.
International Search Report and Written Opinion for International Application No. PCT/US2018/034924, Search completed Sep. 18, 2018, dated Sep. 19, 2018, 15 Pgs.
International Search Report and Written Opinion for International Application No. PCT/US2018/035813, Search completed Dec. 12, 2018, dated Dec. 12, 2018, 11 Pgs.
International Search Report and Written Opinion for International Application PCT/US2013/047950, dated Oct. 8, 2013, Mailed Oct. 10, 2013, 9 pgs.
International Search Report and Written Opinion for International Application PCT/US2014/033510, dated Jan. 8, 2015, Mailed Jan. 8, 2015, 11 Pgs.
International Search Report and Written Opinion for International Application PCT/US2014/056615, dated Dec. 29, 2014, Mailed Dec. 30, 2014, 13 Pgs.
"Corrosion of Titanium and Titanium Alloys", Total Materia, printed Feb. 16, 2016 from http://www.totalmateria.com/Article24.htm, published Sep. 2001, 4 pgs.
"Gear", Dictionary.com. Accessed Aug. 30, 2016, 2 pgs.
"Group 4 element", Wikipedia. https://en.wikipedia.org/wiki/Group_4_element. Published Jun. 11, 2010. Accessed Aug. 24, 2016, 6 pgs.
"Harmonic Drive AG", website, printed from http://harmoncdrive.aero/?idcat=471, Feb. 20, 2014, 2 pgs.
"Harmonic Drive Polymer GmbH", printed from http://www.harmonicdrive.de/English/the-company/subsidiaries/harmonic-drive-polymer-gmbh.html, Feb. 20, 2014, 1 pg.
"Introduction to Thermal Spray Processing", ASM International, Handbook of Thermal Spray Technology (#06994G), 2004, 11 pgs.
Abdeljawad et al., "Continuum Modeling of Bulk Metallic Glasses and Composites", Physical Review Letters, vol. 105, No. 12-17, Sep. 17, 2010, pp. 125503-1-125503-4.
Abrosimova et al., "Crystalline layer on the surface of Zr-based bulk metallic glasses", Journal of Non-Crystalline Solids, vol. 288, Mar. 6, 2001, pp. 121-126.
An et al., "Synthesis of single-component metallic glasses by thermal spray of nanodroplets on amorphous substrates", Applied Physics Letters, vol. 100, Jan. 26, 2012, pp. 041909-1-041909-4.
Anstis et al., "A Critical Evaluation of Indentation Techniques for Measuring Fracture Toughness: I, Direct Crack Measurements", Journal of the American Ceramic Society, vol. 64, No. 9, Sep. 1, 1981, pp. 533-538.
Ashby et al., "Metallic glasses of structural materials", Scripta Materialia, vol. 54, No. 3, Feb. 2006, pp. 321-326.
Bakkal, "Sliding tribological characteristics of Zr-based bulk metallic glass under lubricated conditions", Intermetallics, vol. 18, Mar. 19, 2010, pp. 1251-1253.
Bardt et al., "Micromolding three-dimensional amorphous metal structures", Journal of Materials Research, vol. 22, No. 2, Sep. 2006, pp. 339-343.
Basu et al., "Laser surface coating of Fe—Cr—Mo—Y—B—C bulk metallic glass composition on AISI 4140 steel", Surface & Coatings Technology, vol. 202, Mar. 15, 2008, pp. 2623-2631.
Boopathy et al., "Near-threshold fatigue crack growth in bulk metallic glass composites", Journal of Materials Research, vol. 24, No. 12, Dec. 2009 pp. 3611-3619.
Bordeenithikasem et al., "Glass forming ability, flexural strength, and wear properties of additively manufactured Zr-based bulk metallic glasses produced through laser powder bed fusion", Additive Manufacturing, vol. 21, Mar. 21, 2018, pp. 312-317.
Branagan et al., "Wear Resistant Amorphous and Nanocomposite Steel Coatings", Metallurgical and Materials Transactions A, vol. 32, Oct. 2001, 15 pgs., DOI: 10.1007/s11661-001-0051-8.
Byrne et al., "Bulk Metallic Glasses", Science, vol. 321, Jul. 25, 2008, pp. 502-503.
Cadney et al., "Cold gas dynamic spraying as a method for freeforming and joining materials", Surface & Coatings Technology, vol. 202, Mar. 15, 2008, pp. 2801-2806.
Calin et al., "Improved mechanical behavior of Cu—Ti-based bulk metallic glass by in situ formation of nanoscale precipitates", Scripta Materialia, vol. 48, No. 6, Mar. 17, 2003, pp. 653-658.

(56) References Cited

OTHER PUBLICATIONS

Chen et al., "Elastic Constants, Hardness and Their Implications to Flow Properties of Metallic Glasses", Journal of Non-Crystalline Solids, vol. 18, No. 2, Sep. 1975, pp. 157-171.
Chen et al., "Formation of Micro-Scale Precision Flexures Via Molding of Metallic Glass", Proceedings of the 21$^{st}$ Annual ASPE Meeting, Monterey, CA, 2006, 4 pgs.
Chen et al., "Influence of laser surface melting on glass formation and tribological behaviors of Zr55Al10Ni5Cu30 alloy", Journal of Materials Research, vol. 26, No. 20, Oct. 28, 2011, pp. 2642-2652.
Cheng et al., "Characterization of mechanical properties of FeCrBSiMnNbY metallic glass coatings", Journal of Materials Science, Jul. 1, 2009, vol. 44, pp. 3356-3363.
Cheng et al., "Correlation of the microstructure and mechanical properties of Zr-based in-situ bulk metallic glass matrix composites", Intermetallics, vol. 18, No. 12, Sep. 24, 2010, pp. 2425-2430.
Choi et al., "Tribological behavior of the kinetic sprayed Ni59Ti16Zr20Si2Sn3 bulk metallic glass", Journal of Alloys and Compounds, vol. 434-435, May 31, 2007, pp. 64-67.
Conner et al., "Shear band spacing under bending of Zr-based metallic glass plates", Acta Materialia, vol. 52, No. 8, May 3, 2004, pp. 2429-2434.
Conner et al., "Shear bands and cracking of metallic glass plates in bending", Journal of Applied Physics, vol. 94, No. 2, Jul. 15, 2003, pp. 904-911.
Dai et al., "A new centimeter-diameter Cu-based bulk metallic glass", Scripta Materialia, vol. 54, No. 7, Apr. 2006, pp. 1403-1408.
Dai et al., "High-performance bulk Ti—Cu—Ni—Sn—Ta nanocomposites based on a dendrite-eutectic microstructure", Journal of Materials Research, vol. 19, No. 9, Sep. 2004, pp. 2557-2566.
Davis, "Hardness/Strength Ratio of Metallic Glasses", Scripta Metallurgica, vol. 9, No. 4, 1975, pp. 431-435.
De Beer et al., "Surface Folds Make Tears and Chips", Physics, vol. 5, No. 100, Sep. 4, 2012, 3 pgs.
Demetriou et al., "Glassy steel optimized for glass-forming ability and toughness", Applied Physics Letters, vol. 95, No. 4, Jul. 31, 2009, pp. 041907-1-041907-3; http:/idx.doi.org/10.1063/1.3184792.
Dislich et al., "Amorphous and Crystalline Dip Coatings Obtained from Organometallic Solutions: Procedures, Chemical Processes and Products", Metallurgical and Protective Coatings, vol. 77, 1981, pp. 129-139.
Duan et al., "Lightweight Ti-based bulk metallic glasses excluding late transition metals", Scripta Materialia, vol. 58, No. 6, Mar. 2008, pp. 465-468.
Duan et al., "Tribological properties of Zr41.25Ti13.75Ni10Cu12.5Be22.5 bulk metallic glasses under different conditions", Journal of Alloys and Compounds, vol. 528, Jul. 5, 2012, pp. 74-78.
Fan et al., "Metallic glass matrix composite with precipitated ductile reinforcement", Applied Physics Letters, vol. 81, No. 6, Aug. 5, 2002, pp. 1020-1022.
Fleury et al., "Tribological properties of bulk metallic glasses", Materials Science and Engineering A, vol. 375-377, Jul. 2004, pp. 276-279.
Fornell et al., "Enhanced mechanical properties and in vitro corrosion behavior of amorphous and devitrified Ti40Zr10Cu38Pd12 metallic glass", Journal of the Mechanical Behavior of Biomedical Materials, vol. 4, No. 8, Nov. 2011, pp. 1709-1717.
Fu et al., "Sliding behavior of metallic glass Part I. Experimental investigations", Wear, vol. 250, No. 1-12, Oct. 2001, pp. 409-419.
Ganesan et al., "Bonding behavior studies of cold sprayed copper coating on the PVC polymer substrate", Surface & Coatings Technology, vol. 207, Aug. 25, 2012, pp. 262-269.
Garrett et al., "Effect of microalloying on the toughness of metallic glasses", Applied Physics Letter, vol. 101, Dec. 12, 2012, 241913-1-241913-3.
Gleason Corporation, "Gear Product News", Introducing genesis, The Next Generation in Gear Technology, Apr. 2006, 52 pgs.
Gloriant, "Microhardness and abrasive wear resistance of metallic glasses and nanostructured composite materials", Journal of Non-Crystalline Solids, vol. 316, No. 1, Feb. 2003, pp. 96-103.
Greer, "Partially or fully devitrified alloys for mechanical properties", Materials and Science and Engineering A, vol. 304, May 31, 2001, pp. 68-72.
Greer et al., "Wear resistance of amorphous alloys and related materials", International Materials Reviews, vol. 47, No. 2, pp. 87-112.
Gu et al., "Selective Laser Melting Additive Manufacturing of Ti-Based Nanocomposites: The Role of Nanopowder", Metallurgical and Materials Transactions A, vol. 45, Jan. 2014, pp. 464-476.
Guo et al., "Tensile ductility and necking of metallic glass", Nature Materials, vol. 6, Oct. 2007, pp. 735-739.
Ha et al., "Tensile deformation behavior of two Ti-based amorphous matrix composites containing ductile β dendrites", Materials Science and Engineering A, vol. 552, Aug. 30, 2012, pp. 404-409.
Hale, "Principles and Techniques for Designing Precision Machines", Ph.D. Thesis, Feb. 1999, 493 pgs.
Harmon et al., "Anelastic to Plastic Transition in Metallic Glass-Forming Liquids", Physical Review Letters, vol. 99, Sep. 28, 2007, 135502-1-135502-4.
Haruyama et al., "Volume and enthalpy relaxation in Zr55Cu30Ni5Al10 bulk metallic glass", Acta Materialia, vol. 58, No. 5, Mar. 2010, pp. 1829-1836.
Hays et al., "Microstructure Controlled Shear Band Pattern Formation and Enhanced Plasticity of Bulk Metallic Glasses Containing in situ Formed Ductile Phase Dendrite Dispersions", Physical Review Letters, vol. 84, No. 13, Mar. 27, 2000, pp. 2901-2904.
He et al., "Novel Ti-base nanostructure—dendrite composite with enhanced plasticity", Nature Materials, vol. 2, Jan. 2003, Electronic Publication: Dec. 8, 2002, pp. 33-37, doi: 10.1038/nmat792.
Hejwowski et al., "A comparative study of electrochemical properties of metallic glasses and weld overlay coatings", Vacuum, vol. 88, Feb. 2013, pp. 118-123.
Hofmann, "Bulk Metallic Glasses and Their Composites: A Brief History of Diverging Fields", Journal of Materials, vol. 2013, Jan. 10, 2013, 8 pgs.
Hofmann, "Shape Memory Bulk Metallic Glass Composites", Science, vol. 329, No. 5997, Sep. 10, 2010, pp. 1294-1295.
Hofmann et al., "Designing metallic glass matrix composites with high toughness and tensile ductility", Nature Letters, vol. 451, Feb. 28, 2008, pp. 1085-1090.
Hofmann et al., "Development of tough, low-density titanium-based bulk metallic glass matrix composites with tensile ductility", PNAS, vol. 105, No. 51, Dec. 23, 2008, pp. 20136-20140.
Hofmann et al., "Improving Ductility in Nanostructured Materials and Metallic Glasses: Three Laws", Materials Science Forum, vol. 633-634, 2010, pp. 657-663.
Hofmann et al., "Semi-solid Induction Forging of Metallic Glass Matrix Composites", JOM, vol. 61, No. 12, Dec. 2009, pp. 11-17, plus cover.
Hong et al., "Microstructural characteristics of high-velocity oxygen-fuel (HVOF) sprayed nickel-based alloy coating", Journal of Alloys and Compounds, vol. 581, Dec. 25, 2013, pp. 398-403.
Hu et al., "Crystallization Kinetics of the Cu47.5Zr47.5Al5 Bulk Metallic Glass under Continuous and Iso-thermal heating", Applied Mechanics and Materials, vol. 99-100, Sep. 8, 2011, pp. 1052-1058.
Huang et al., "Dendritic microstructure in the metallic glass matrix composite Zr56Ti14Nb5Cu7Ni6Be12", Scripta Materialia, vol. 53, No. 1, Jul. 2005, pp. 93-97.
Huang et al., "Fretting wear behavior of bulk amorphous steel", Intermetallics, vol. 19, No. 10, Oct. 2011, pp. 1385-1389.
Inoue et al., "Cobalt-based bulk glassy alloy with ultrahigh strength and soft magnetic properties", Nature Letters, vol. 2, Oct. 2003, pp. 661-663.
Inoue et al., "Development and applications of late transition metal bulk metallic glasses", Bulk Metallic Glasses, 2008, pp. 1-25.
Inoue et al., "Developments and applications of bulk metallic glasses", Reviews on Advanced Materials Science, vol. 18, Feb. 28, 2008, pp. 1-9.

(56) References Cited

OTHER PUBLICATIONS

Inoue et al., "Preparation of 16 mm Diameter Rod of Amorphous Zr65Al7.5Ni10Cu17.5 Alloy", Material Transactions, JIM, vol. 34, No. 12, 1993, pp. 1234-1237.
Inoue et al., "Recent development and application products of bulk glassy alloys", Acta Materialia, vol. 59, No. 6, Apr. 2011, pp. 2243-2267.
Ishida et al., "Wear resistivity of super-precision microgear made of Ni-based metallic glass", Materials Science and Engineering A, vol. 449-451, Mar. 25, 2007, pp. 149-154.
Jiang et al., "Low-Density High-Strength Bulk Metallic Glasses and Their Composites: A Review", Advanced Engineering Materials, vol. 17, No. 6, Nov. 19, 2014, pp. 1-20, DOI: 10.1002/adem. 201400252.
Jiang et al., "Tribological Studies of a Zr-Based Glass-Forming Alloy with Different States", Advanced Engineering Materials, vol. 11, No. 11, Nov. 18, 2009, pp. 925-931.
Johnson et al., "Quantifying the Origin of Metallic Glass Formation", Nature Communications, Jan. 20, 2016, vol. 7, No. 10313, 7 pgs. doi: 10.1038/ncomms10313.
Jung et al., "Fabrication of Fe-based bulk metallic glass by selective laser melting: A parameter study", Materials and Design, vol. 86, Jul. 30, 2015, pp. 703-708.
Kahraman et al., "A Feasibility Study on Development of Dust Abrasion Resistant Gear Concepts for Lunar Vehicle Gearboxes", NASA Grant NNX07AN42G Final Report, Mar. 11, 2009, 77 pgs.
Kim et al., "Amorphous phase formation of Zr-based alloy coating by HVOF spraying process", Journal of Materials Science, vol. 36, 2001, pp. 49-54.
Kim et al., "Enhancement of metallic glass properties of Cu-based BMG coating by shroud plasma spraying", Surface & Coatings Technology, Jan. 25, 2011, vol. 205, pp. 3020-3026.
Kim et al., "Oxidation and crystallization mechanisms in plasma-sprayed Cu-based bulk metallic glass coatings", Acta Materialia., vol. 58, Feb. 1, 2010, pp. 952-962.
Kim et al., "Production of Ni65Cr15P16B4 Metallic Glass-Coated Bipolar Plate for Fuel Cell by High Velocity Oxy-Fuel (HVOF) Spray Coating Method", The Japan Institute of Metals, Materials Transactions, vol. 51, No. 9, Aug. 25, 2010, pp. 1609-1613.
Kim et al., "Realization of high tensile ductility in a bulk metallic glass composite by the utilization of deformation-induced martensitic transformation", Scripta Materialia, vol. 65, May 3, 2011, pp. 304-307.
Kim et al., "Weldability of Cu54Zr22Ti18Ni6 bulk metallic glass by ultrasonic welding processing", Materials Letters, vol. 130, Sep. 1, 2014, pp. 160-163.
Kobayashi et al., "Fe-based metallic glass coatings produced by smart plasma spraying process", Materials Science and Engineering B, vol. B148, No. 1-3, Feb. 25, 2008, pp. 110-113.
Kobayashi et al., "Mechanical property of Fe-base metallic glass coating formed by gas tunnel type plasma spraying", Surface & Coatings Technology, vol. 202, No. 12, Mar. 15, 2008, 6 pgs.
Kobayashi et al., "Property of Ni-Based Metallic Glass Coating Produced by Gas Tunnel Type Plasma Spraying", International Plasma Chemistry Society, ISPC 20, 234, Philadelphia, USA, Retrieved from: http://www.ispc-conference.org/ispcproc/ispc20/234.pdf, Jul. 24, 2011, 4 pgs.
Kong et al., "Effect of Flash Temperature on Tribological Properties of Bulk Metallic Glasses", Tribology Letters, vol. 35, Apr. 25, 2009, pp. 151-158.
Kozachkov et al., "Effect of cooling rate on the volume fraction of B2 phases in a CuZrAlCo metallic glass matrix composite", Intermetallics, vol. 39, Aug. 2013, pp. 89-93.
Tao et al., "Effect of rotational sliding velocity on surface friction and wear behavior in Zr-based bulk metallic glass", Journal of Alloys and Compounds, vol. 492, No. 1-2, Mar. 4, 2010, pp. L36-L39.
Tao et al., "Influence of isothermal annealing on the micro-hardness and friction property in CuZrAl bulk metallic glass", Advanced Materials Research, vol. 146-147, 2011, pp. 615-618.

Tobler et al., "Cryogenic Tensile, Fatigue, and Fracture Parameters for a Solution-Annealed 18 Percent Nickel Maraging Steel", Journal of Engineering Materials and Technology, Apr. 1978, vol. 100, pp. 189-194.
Wagner, "Mechanical Behavior of 18 Ni 200 Grade Maraging Steel at Cyrogenic Temperatures", J Aircraft, vol. 23, No. 10, Oct. 1986, pp. 744-749.
Wang et al., "Progress in studying the fatigue behavior of Zr-based bulk-metallic glasses and their composites", Intermetallics, vol. 17, No. 8, Aug. 2009, pp. 579-590.
Wikipedia, "Harmonic Drive", printed Feb. 20, 2014, 4 pgs.
Wu et al., "Bulk Metallic Glass Composites with Transformation-Mediated Work-Hardening and Ductility", Advanced Materials, vol. 22, No. 25, Jul. 7, 2010, pp. 2770-2773.
Wu et al., "Dry Sliding tribological behavior of Zr-based bulk metallic glass", Transactions of Nonferrous Metals Society of China, vol. 22, No. 3, Mar. 2012, pp. 585-589.
Wu et al., "Effects of environment on the sliding tribological behaviors of Zr-based bulk metallic glass", Intermetallics, vol. 25, Jun. 2012, pp. 115-125.
Wu et al., "Formation of Cu—Zr—Al bulk metallic glass composites with improved tensile properties", Acta Materialia, vol. 59, No. 8, May 2011, pp. 2928-2936.
Wu et al., "Use of rule of mixtures and metal volume fraction for mechanical property predictions of fibre-reinforced aluminum laminates", Journal of Materials Science, vol. 29, 1994, pp. 4583-4591.
Yin et al., "Microstructure and mechanical properties of a spray-formed Ti-based metallic glass former alloy", Journal of Alloys and Compounds, vol. 512, No. 1, Jan. 25, 2012, pp. 241-245.
Zachrisson et al., "Effect of Processing on Charpy impact toughness of metallic glass matrix composites", Journal of Materials Research, vol. 26, No. 10, May 28, 2011, pp. 1260-1268.
Zhang et al., "Abrasive and corrosive behaviors of Cu—Zr—Al—Ag—Nb bulk metallic glasses", Journal of Physics: Conference Series, The 13th International Conference on Rapidly Quenched and Metastable Materials, vol. 144, Jan. 1, 2009, pp. 1-4.
Zhang et al., "Robust hydrophobic Fe-based amorphous coating by thermal spraying", Applied Physics Letters, vol. 101, No. 12, Sep. 20, 2012, pp. 121603-1-121603-4.
Zhang et al., "Wear behavior of a series of Zr-based bulk metallic glasses", Materials Science and Engineering A, vol. 475, No. 1-2, Feb. 25, 2008, pp. 124-127.
Zhou et al., "Microstructure and Electrochemical Behavior of Fe-Based Amorphous Metallic Coatings Fabricated by Atmospheric Plasma Spraying", Journal of Thermal Spray Technology, vol. 20, No. 1-2, Jan. 2011, pp. 344-350.
Zhu et al., "Ta-particulate reinforced Zr-based bulk metallic glass matrix composite with tensile plasticity", Scripta Materialia, vol. 62, No. 5, Mar. 2010, pp. 278-281.
Zhuo et al., "Spray formed Al-based amorphous matrix nanocomposite plate", Journal of Alloys and Compounds, vol. 509, No. 18, May 5, 2011, pp. L169-L173.
Extended European Search Report for European Application No. 18806700.3, Search completed Oct. 20, 2020, dated Oct. 28, 2020, 7 Pgs.
Extended European Search Report for European Application No. 18809486.6, Search completed Sep. 30, 2030, dated Oct. 12, 2020, 7 Pgs.
Adharapurapu et al., "Fracture of Ti—Al3Ti metal-intermetallic laminate composites: Effects of lamination on resistance-curve behavior", Metallurgical and Materials Transactions A, Nov. 2005, vol. 36A, 3217-3236.
Berger, "A Survey of Additive Manufacturing Processes Applied on the Fabrication of Gears", 1st International Conference on Progress in Additive Manufacturing (Pro-AM 2014), May 26-28, 2014, pp. 315-320, doi: 10.3850/978-981-09-0446-3_010.
Kim et al., "Design and synthesis of Cu-based metallic glass alloys with high glass forming ability", Journal of Metastable and Nanocrystalline Materials, Sep. 1, 2005, vols. 24-25, pp. 93-96, doi:10.4028/www.scientific.net/JMNM.24-25.93.
Kumar et al., "Embrittlement of Zr-based Bulk Metallic Glasses", Science Direct, Acta Materialia, 2009, vol. 57, pp. 3572-3583, available online May 11, 2009, doi:10.1016/j.actamat.2009.04.16.

(56) References Cited

OTHER PUBLICATIONS

Lu et al., "Crystallization Prediction on Laser Three-Dimensional Printing of Zr-based Bulk Metallic Glass", Journal of Non-Crystalline Solids, 2017, vol. 461, pp. 12-17, available online Jan. 29, 2017, http://dx.doi.org/10.1016/j.jnoncrysol.2017.01.038.

Qiao et al., "Metallic Glass Matrix Composites", Materials Science and Engineering, Feb. 2016, vol. 100, pp. 1-69, http://dx.doi.org.10.10163/jmser.2015.12.001.

Roberts, "Developing and Characterizing Bulk Metallic Glasses for Extreme Applications", XP055731434, Retrieved from the Internet (Dec. 16, 2013): URL:https://thesis.library.caltech.edu/8049/141/Scott_Roberts_thesis_2013_Complete_ Thesis. pdf [retrieved on Sep. 17, 2020].

Whang et al., "Microstructures and age hardening of rapidly quenched Ti—Zr—Si alloys", Journal of Materials Science Letters, 1985, vol. 4, pp. 883-887.

Yao et al., "Fe-Based Bulk Metallic Glass With High Plasticity", Applied Physics Letters, Feb. 5, 2007, vol. 90, 061901, doi: 10.1063/1.2437722.

Yokoyama et al., "Tough Hypoeutectic Zr-Based Bulk Metallic Glasses", Metallurgical and Materials Transactions, Year 2011, vol. 42A, pp. 1468-1475, DOI: 10.1007/s11661-011-0631-1.

Zheng et al., "Processing and Behavior of Fe-Based Metallic Glass Components via Laser-Engineered Net Shaping", Metallurgical and Materials Transactions A, 40A, 1235-1245, DOI: 10.1007/s11661-009-9828-y.

Zhuo et al., "Ductile Bulk Aluminum-Based Alloy with Good Glass-Forming Ability and High Strength", Chinese Physics Letters, 2009, vol. 26, No. 6, pp. 066402-1-066402-4.

\* cited by examiner

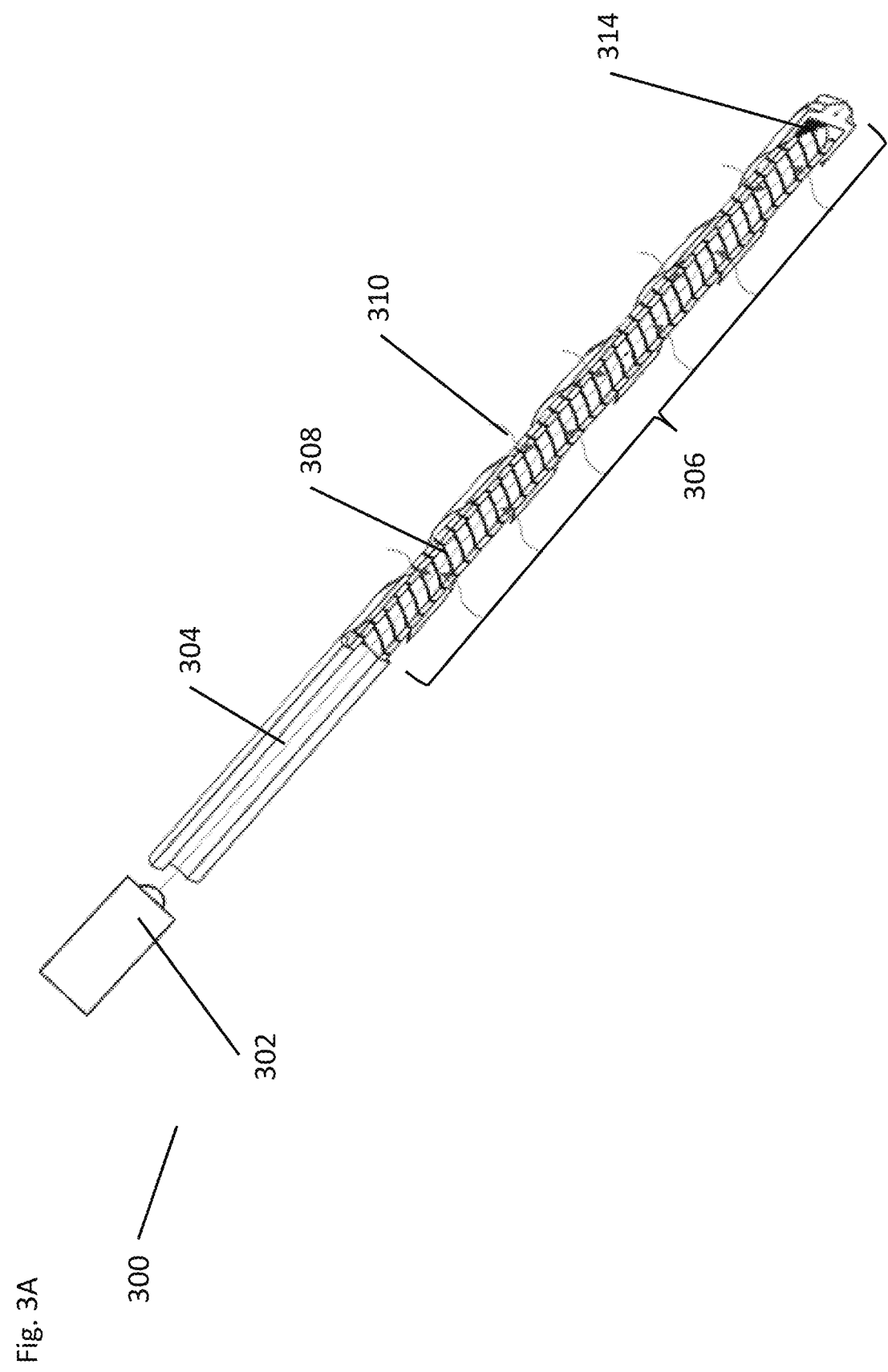

CUTTING TOOL WITH POROUS REGIONS

CROSS-REFERENCED APPLICATIONS

This application claims priority to U.S. Provisional Patent Application No. 62/815,254 filed on Mar. 7, 2019. The enclosure of which is included herein by reference in its entirety.

STATEMENT OF FEDERALLY SPONSORED RESEARCH

This invention was made with government support under Grant No. 80NM0018D004 awarded by NASA (JPL). The government has certain rights in the invention.

FIELD OF THE INVENTION

The present invention generally relates to cutting tools, and more specifically cutting tools that have integrated porous regions, adaptable for in-situ sampling and analysis.

BACKGROUND OF THE INVENTION

A cutting tool is typically described by a shaft that is connected to a rotating element, such as a motor, where the shaft is connected to a cutting element. Some cutting elements are sharp and elongated like a knife and others may be smaller like teeth. Some may be equally positioned on a blade like a saw while others may be spirally connected to a shaft such as drill. In conventional designs, the body that connects the cutting teeth to the shaft is made as rigid as possible to allow the cutting teeth to have maximum engagement with the material being cut without slipping or bending. Moreover, the cutting elements and supporting elements are often made of solid material to provide the necessary strength to cut through a variety of materials without damage to the cutting tool.

Cutting tools have been used in a variety of industries to cut or bore a variety of materials including rock, wood, metal, composite, plastic, etc. Additionally, many cutting tools are used to obtain material samples. For example, during space based exploration missions many scientists wish to take samples of materials, and drilling or cutting tools are often used to break through or grind the material to remove samples for subsequent testing. Obtaining samples in order to study their makeup and composition is challenging process that often involved multiple steps, especially when it involves extraterrestrial samples.

Advancements in space based and scientific technology have increased the need to regularly obtain samples of new materials. Furthermore, the need to ensure the samples are as whole as possible is increasingly important when considering the increased interest in discovering extraterrestrial life. Despite such advancements, many industries continue to use traditional method of sample removal that can often end in less than whole samples.

BRIEF SUMMARY OF THE INVENTION

Many embodiments are directed to a cutting tool that is configured to intake sample materials during the cutting process through a porous section of the tool. The sample material can then be analyzed in-situ and avoid the requirement to stop cutting or drilling in order to take a sample. Many embodiments of the tool have a support region that cooperatively engages with a rotational motor as well as a cutting region with a cutting element and connected to the support region such that a rotation induced from the rotational motor would equate to a corresponding rotation of the cutting region. Many embodiments also include an internal chamber disposed within the cutting tool, wherein the internal chamber connects both the cutting region and the supporting region and wherein the internal chamber has an opening in at least the support region, and a porous region disposed in at least a portion of the cutting or the support region wherein the porous region comprises a plurality of porous elements disposed between a plurality of support elements that interconnect the porous region with the cutting region and the support region, and wherein the porous region receives a sample material through the porous elements and directs the sample material into the internal chamber such that the sample material can be analyzed.

In other embodiments, the tool has an in-situ testing component where the testing component has a light source disposed at the opening of the internal chamber and wherein the light source is configured to project light within the internal chamber towards a reflective element disposed within the internal chamber of the cutting tool, and a detector disposed at the opening of the internal chamber wherein the detector receives a reflected signal from the reflective element.

In still other embodiments, the in-situ testing component is electronically connected to a data analysis element configured to analyze a set of data produced by the detector.

In yet other embodiments, the porous region is made from a material selected from the group consisting of maraging steel, carbon steel, stainless steel, tool steel, precipitation hardened steel, Inconel, Ti-6Al-4V, bulk metallic glass, nickel superalloy, shape memory alloys, Nitinol, and high entropy alloys.

In still yet other embodiments, the porous region is made of a partially sintered metallic component such that the plurality of porous elements allow gas or liquid to permeate through the porous region.

In other embodiments, the internal chamber has a getter material disposed therein such that the getter material is exposed to and interacts with the sample material received through the plurality of porous elements.

In still other embodiments, the tool has a mechanical device disposed within the internal chamber such that the mechanical device can interact with the sample material and move the sample material within the internal chamber.

In yet other embodiments, the mechanical device is selected from a group consisting of an impeller and a screw.

In still yet other embodiments, the cutting portion of the tool contains tungsten-carbide.

In other embodiments, the cutting tool is made from a material selected from the group consisting of iron, nickel, titanium, and zirconium.

In still other embodiments, the internal chamber is configured to receive a fluid material through the opening and wherein the fluid material is pushed through the porous region to the external environment or material being cut.

In yet other embodiments, the support region, the cutting region, and the porous region have the same material composition.

In still yet other embodiments, the support region, the cutting region, and the porous region have different material compositions.

In other embodiments, the plurality of porous elements range in size from 100 nm to 1 mm.

In still other embodiments, the cutting tool has an extraction hole that is disposed within the support region and interconnects with the internal chamber, wherein the extraction hole is connected to an external analysis device that receives at least a portion of the sample material from within the internal chamber for analysis.

In yet other embodiments, the analysis is done by spectrometry.

In still yet other embodiments, the cutting tool has a plurality of cutting regions wherein each of the plurality of cutting regions is each connected to the support element and wherein each of the plurality of cutting regions has a correlating internal chamber that interconnects to an internal chamber of the support region.

In other embodiments, the porous region is disposed in at least a portion of each of the plurality of cutting regions.

In still other embodiments, the tool is manufactured using an additive manufacturing process.

In yet other embodiments, the additive manufacturing process is selected from a group consisting of powder bed fusion, directed energy deposition, ultrasonic additive manufacturing, binder jetting, material jetting, cold spraying, friction welding, and material extrusion.

Other embodiments include a method for material extraction and analysis where the method uses a material cutting tool that has a support region that cooperatively engages with a rotational motor and a cutting region with a cutting element and connected to the support region such that a rotation induced from the rotational motor would equate to a corresponding rotation of the cutting region. The cutting tool also has an internal chamber disposed within the cutting tool, wherein the internal chamber connects both the cutting region and the supporting region and wherein the internal chamber has an opening in at least the support region and a porous region disposed in at least a portion of the cutting or the support region wherein the porous region comprises a plurality of porous elements disposed between a plurality of support elements that interconnect the porous region with the cutting region and the support region. The method also includes receiving a sample material through the porous elements and directing the sample material into the internal chamber of the tool. Additionally, the method may include projecting a signal from an imaging device towards the internal chamber wherein the signal can interact with the sample material and produce a reflective signal wherein the reflective signal is received by a signal detector. Finally, the method may process the reflective signal to determine the material type and composition.

Additional embodiments and features are set forth in part in the description that follows, and in part will become apparent to those skilled in the art upon examination of the specification or may be learned by the practice of the disclosure. A further understanding of the nature and advantages of the present disclosure may be realized by reference to the remaining portions of the specification and the drawings, which forms a part of this disclosure.

BRIEF DESCRIPTION OF THE DRAWINGS

The description will be more fully understood with reference to the following figures, which are presented as exemplary embodiments of the invention and should not be construed as a complete recitation of the scope of the invention, wherein:

FIG. 3A illustrates a cross sectional view of a drill bit with an imaging device positioned at one end of the bit in accordance with the embodiments of the invention.

DETAILED DESCRIPTION OF THE INVENTION

Turning now to the drawings, many embodiments are directed to a cutting tool adapted for removing material samples such that portions of the sample can be retrieved via porous regions disposed in portions of the cutting tool. In many embodiments, the cutting tool may be a drill bit with a cutting surface spirally located along the length of the bit where at least a portion of the bit is a porous region. The porous region, in accordance with many embodiments, may be capable of accepting portions of a sample material for additional testing and analysis. Many embodiments, may be configured to provide in-situ analysis of the sample material. For example, many embodiments may have internal and external components that allow for the samples to be analyzed during the drilling process that would allow drilling or cutting to continue without interruption. Such embodiments can save valuable time and money.

Drilling and coring rocks to study their makeup and composition is a challenging, multi-stepped process; especially when doing it on extraterrestrial bodies. Generally evaluating the composition of a rock involves cutting into the surface, breaking off a core sample, delivering that sample to an instrument, in some cases on-board a spacecraft, and then waiting for the analysis. If something of interest is discovered, it is nearly impossible to go back into the same hole to collect a second sample, this is even more important and true with respect to extraterrestrial samples. Additionally, if there are trapped volatiles, such as water or gasses in the rocks, these can get lost due to an inability to trap them during the drilling process. This can be especially true when considering the challenges of drilling on an icy world, heating of the sample due to the warmth of the tool or friction between the tool and the surface could result in significant loss of sample delivered to the instruments on-board the spacecraft.

Performing analysis on a sample while in the process of drilling or cutting could eliminate the need to extract the tool to remove a sample, thereby allowing the tool to proceed deeper into the sample. Additionally, analyzing the material while the tool is still in the hole could be key in looking at stratifications of surface layers due to the repeated deposition of material over time (e.g. deposition of ice/water from icy geysers on icy worlds such as Enceladus). However, many sampling methods used today continue to use more traditional drilling and cutting tools and therefore result in potential loss of sample integrity and process efficiency. However, many embodiments enable a tool to be adaptable to perform in-situ sample analysis during drilling or cutting operation such as capturing gas, liquid, or solid samples during the removal process.

Figure 1:
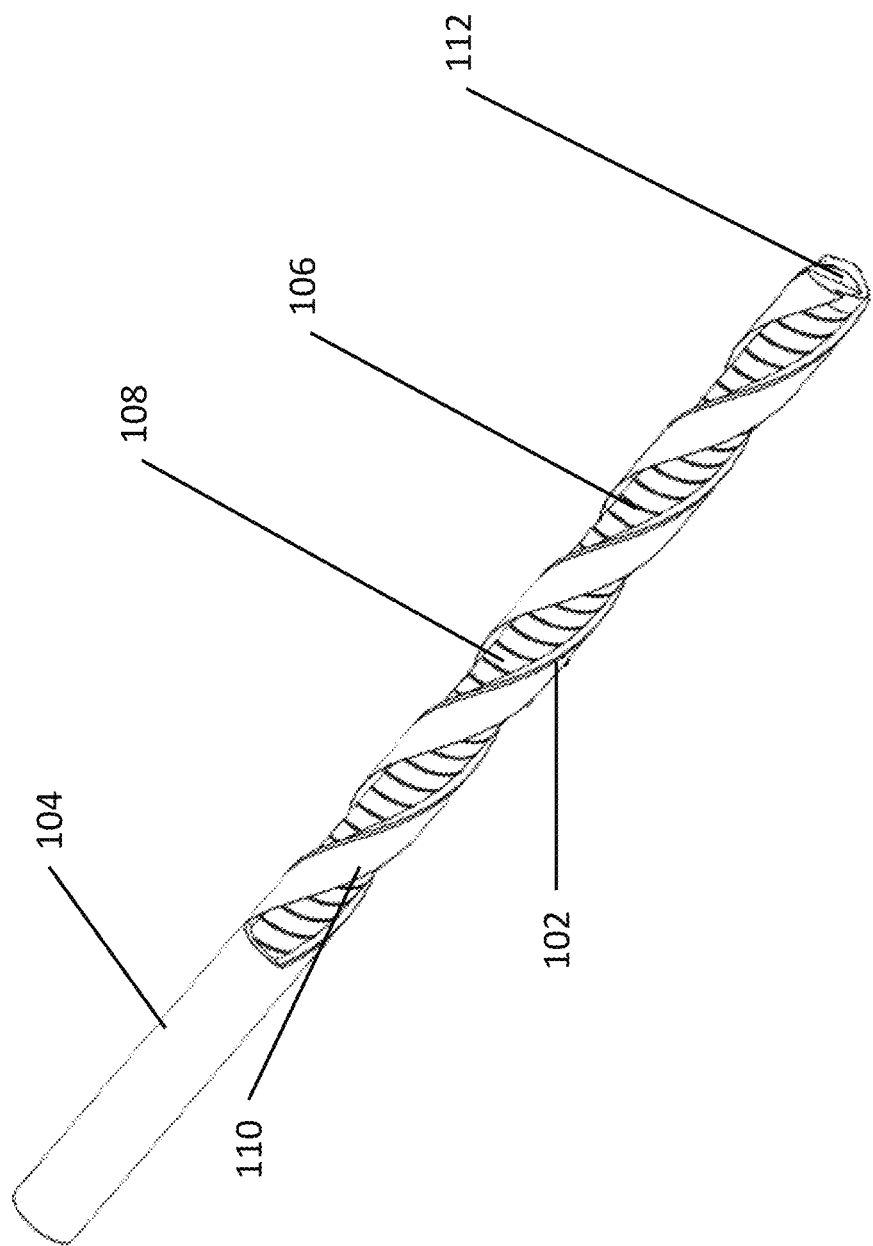
FIG. 1 illustrates a drill bit with integrated porous regions in accordance with embodiments of the invention.

Turning now to the figures, cutting tools with porous portions suitable for ins-situ material analysis are shown. FIG. 1 illustrates a drill bit type cutting tool 100 with a cutting portion 102 the spirals along the length of an elongated shaft 104. The spiraling cutting portion 102, as with many drill bits, helps to remove cut material from the hole. In many embodiments, portions of the shaft 104 may be made up of multiple porous regions 106 that run the cutting length of the shaft. In many embodiments, the porous regions 106 may be interspersed between strengthening sections 108 of material. The strengthening sections, in many embodiments, can provide additional support to the tool 100 during the cutting/drilling process to prevent loads from damaging the tool as well as an internal sampling chamber (not shown). Additionally, the spiral cutting surface 102 may have a widened surface 110 that can add strength to the drill 100 similar to the strengthening sections 108 to prevent damage from longitudinal and side loads. In many embodiments, the cutting surface 102 can be sharpened similar to a traditional drill bit. Likewise, similar to many traditional drill bits, the tip 112 of many embodiments can be sharpened to improve the cutting capabilities of the tool 100. Although a drill bit is illustrated, it should be understood that the basic elements can be implemented in a number of embodiments.

Figure 2:
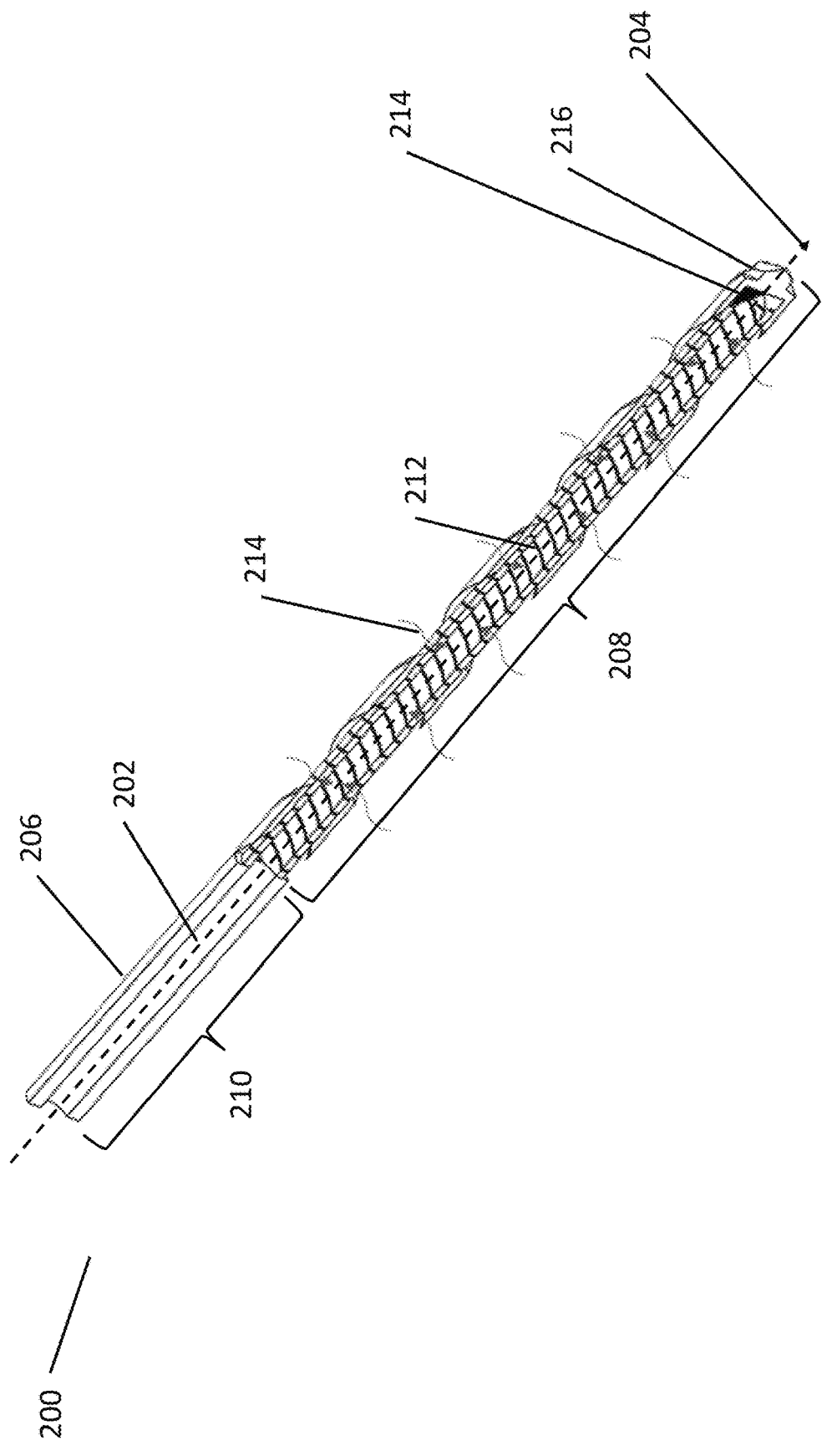
FIG. 2 illustrates a cross sectional view of a drill bit with integrated porous regions that run along a central opening in accordance with embodiments of the invention.

Turning now to FIG. 2, an embodiment of a cutting tool that has a hollowed out center section is shown. In accordance with many embodiments, the cutting tool 200 may have a hollowed out portion or inner chamber 202 that runs along the length of a central axis 204. In some embodiments, the inner chamber 202 may make up only a portion of the length of the shaft 206 while in other embodiments, the chamber 202 may run the majority of the length of the shaft 206. In accordance with many embodiments, similar to those illustrated in FIG. 1, the shaft 206 may have multiple sections such as a cutting section 208 and a solid or stiffer support section 210 for connecting the tool 200 to a mechanical device such as a motor. Likewise, in many embodiments, the cutting section 208 may have porous regions 212 that make up at least a portion of the cutting section such that it can be exposed to the material that is being cut. Moreover, the porous regions 212 may be configured to extract or accept samples 214 from the material being cut and direct them into the inner chamber 202 of the tool. In accordance with many embodiments, the porous regions 212 may be made up of a number of pores that range in size from 100 nm to 1 mm in diameter. The porous region, in accordance with many embodiments, can allow for materials such as gasses and/or liquids to wick or move across the outer portion of the tool into the inner portion or inner chamber 202 and thus be captured within the tool for further testing and sampling.

In accordance with some embodiments, the tool 200 may be configured with one or more additional elements that can be used to aid in the testing of the material. In some embodiments, the inner chamber 202 may have a reflective element 214 positioned within the inner chamber 202 at the tip 216 of the tool. The reflective element 214 may be a mirror or any other type of reflective element that can be used in conjunction with a light source and other components to help determine the composition of the sample material 214. In some embodiments, the reflective element 214 may be positioned at an angle with respect to the inner walls of the inner chamber 202. In other embodiments, the reflective element 214 may be positioned flat on the end portion of the inner chamber 202.

Referring to FIG. 3A, an embodiment of a cutting tool 300 similar to embodiments described in FIGS. 1 and 2 is shown. In accordance with some embodiments, the cutting tool 300 may be configured to aid in in-situ material analysis with one or more components. For example, in some embodiments, the cutting tool may be outfitted with an imaging device 302 positioned at one end of the tool 300 where it is open to the inner chamber 304. In some embodiments the imaging source may be a light emitter/receiver configured to project light down the inner chamber 304 towards the cutting portion 306 or the area of the tool with porous sections 308. This directed light can be done in a number of manners depending on the configuration of the tool. For example, in some embodiments the tool 300 may have an elongated inner chamber 304 for which light can be projected in a single direction. However, if the inner chamber is not a straight shaft then one or more reflective elements can be used to direct the light to the imaging device and/or the porous regions 308 In accordance with many embodiments, the imaging device 302 may be configured analyze received images to determine the type and concentration of the material.

Figure 3B:
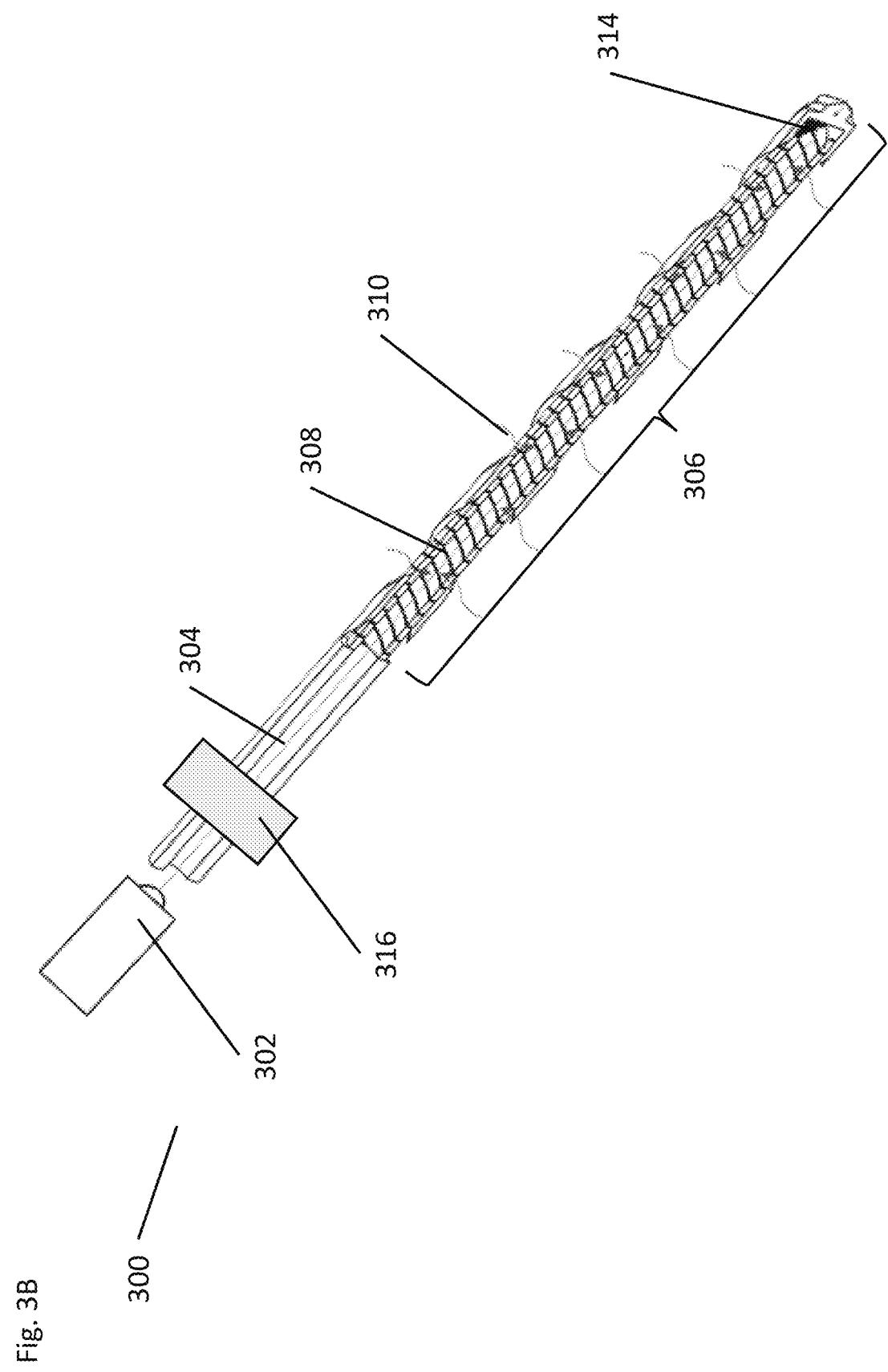
FIG. 3B illustrates a cross sectional view of a drill bit with an imaging device and a power supply in accordance with the embodiments of the invention.

Turning now to FIG. 3B, in many embodiments the imaging device may be an IR receiver that works in conjunction with an IR transmitter 314. In some embodiments the IR transmitter may be a resistive heater. In many embodiments the IR transmitter may work to transmit an IR signal along the inner chamber such that it passes through the received material. Accordingly, the imaging device can detect the IR signal and analyze the signal for material type and composition. Likewise, many embodiments may be able to perform in-situ analysis on the material samples. In some embodiments, the IR transmitter 314 may be powered by a separate power source 316. In many embodiments, the power source 316 may be a slip ring positioned at one end of the tool. In other embodiments the power source may be integrated with the imaging device 302 and configured to transmit power to the emitter 314.

Figure 4:
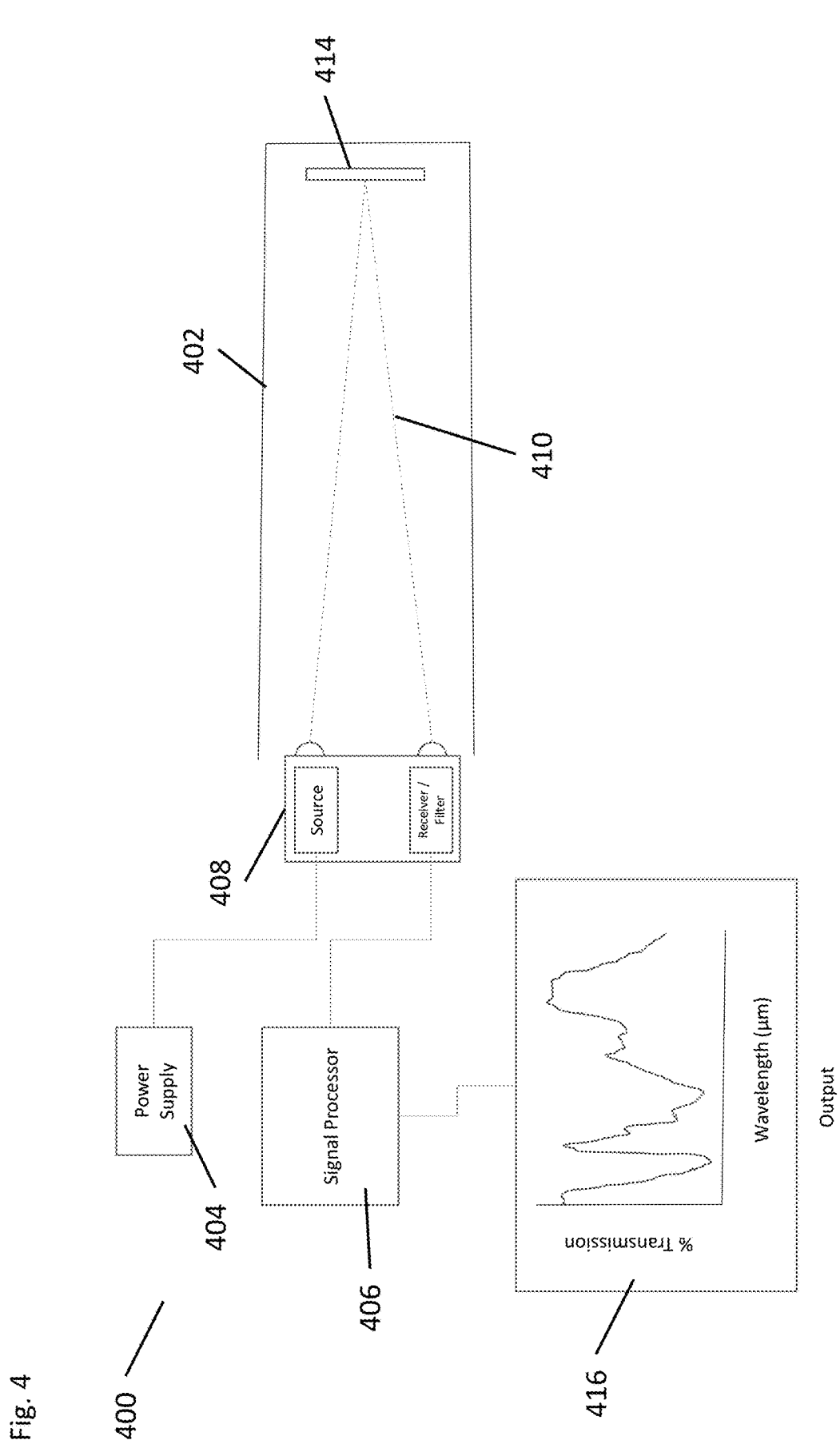
FIG. 4 illustrates a schematic view of a material analysis system in accordance with embodiments of the invention.

Referring now to FIG. 4, many embodiments may incorporate additional components as part of a system 400 in order to perform the analysis of the material samples. For example, in some embodiments the cutting tool 402 may have an exterior power source 404 and signal processor 406 connected to the imaging device 408. The imaging device may be powered by the power source 404 to direct and receive a signal 410 into the tool 402. As described above, many embodiments may have a reflector/transmitter 414 positioned at one end of the tool 402 to reflect and/or transmit the signal 410 towards the imaging device 408. In accordance with many embodiments, the system 400 may have an external output device 416 such as a computer system or user interface system connected to the signal processor 406. The signal processer, in many embodiments can analyze the signal 410 and transmit the results to the output device 416 for use. In accordance with many embodiments, the output device 416 can be remotely accessed by the user or may be remotely connected to the system 400 such that the user may not be required to be close to the tool 402 during operation. Such examples may include onboard a spacecraft while the tool 402 is performing the drilling operation in a remote location.

Figure 5A:
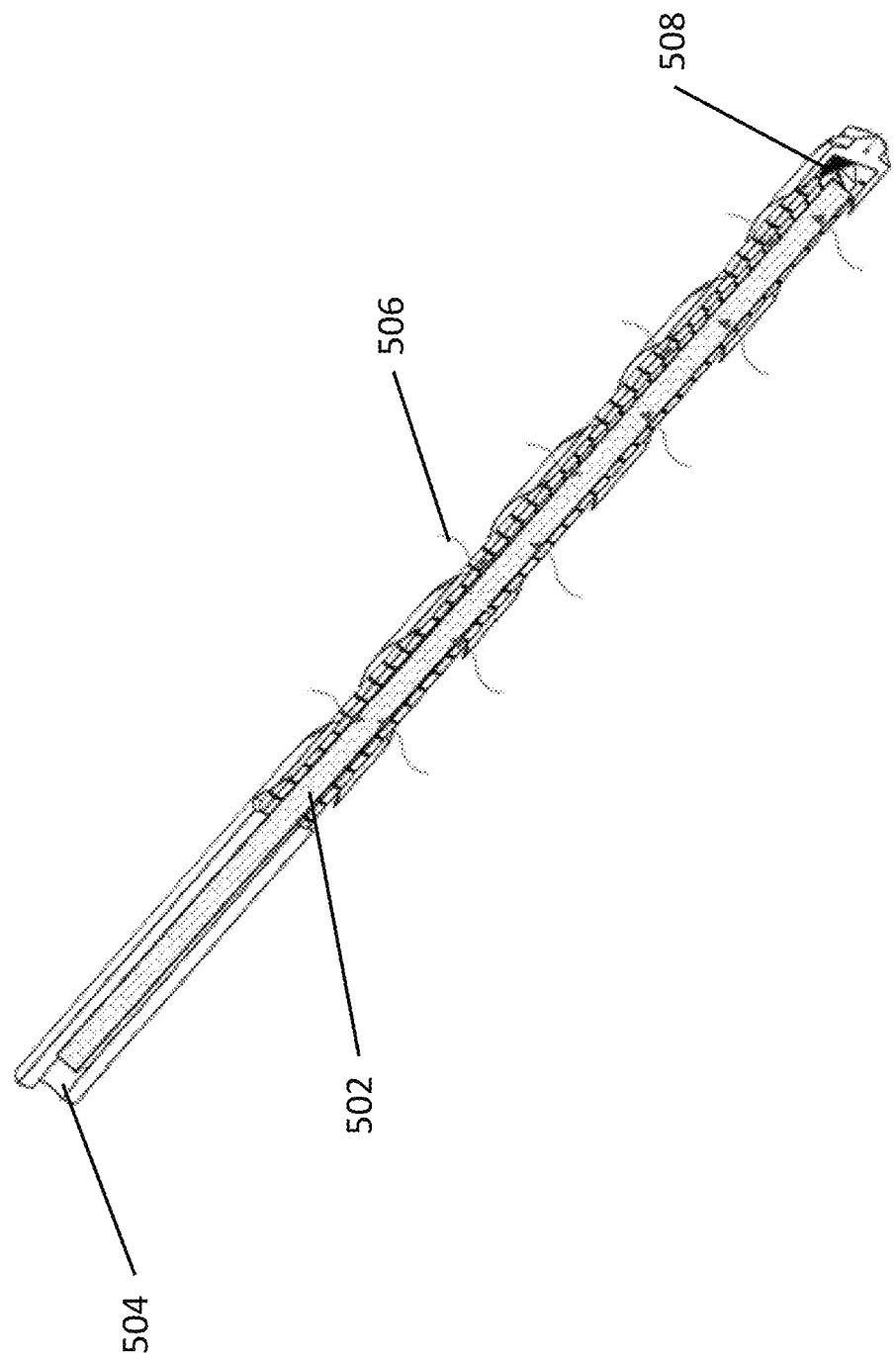
FIG. 5A illustrates a cross sectional view of a drill bit with a getter material centrally disposed in accordance with embodiments of the invention.

Turning now to FIG. 5A, other embodiments of the cutting tool may incorporate additional methods of material collection and analysis. For example, in some embodiments, the cutting tool 500 may have a getter material 502 that is placed along the length of the inner chamber 504. A getter material is a substance of reactive material that can be placed inside a system capable of maintaining vacuum. When a substance interacts with the getter material it combines by absorption or through a chemical reaction occurs. The reacted substance can then be removed and analyzed. In accordance with many embodiments, the getter material 502 can be removed through the open end 506 of the inner chamber 504 to be analyzed. In accordance with many embodiments, the getter material 502 may be customized to match the potential substances to be analyzed, such as desiccants for absorbing water or materials similar to Tenax® for trapping volatiles. Additionally, many embodiments may allow for in-process exchange of the getter material 502 to perform additional tests as the cutting tool is driven deeper into the sampling material. Accordingly, many embodiments may incorporate getter material removal tools and on-board analysis components that are connected to the machine operating the cutting tool. In some embodiments, the getter material 502 can be removed and placed into a Gas Chromatograph Mass Spectrometer oven (GCMS) for further analysis. Embodiments of the process of removing the getter material 502 can be further illustrated in FIG. 5B.

Figure 5B:
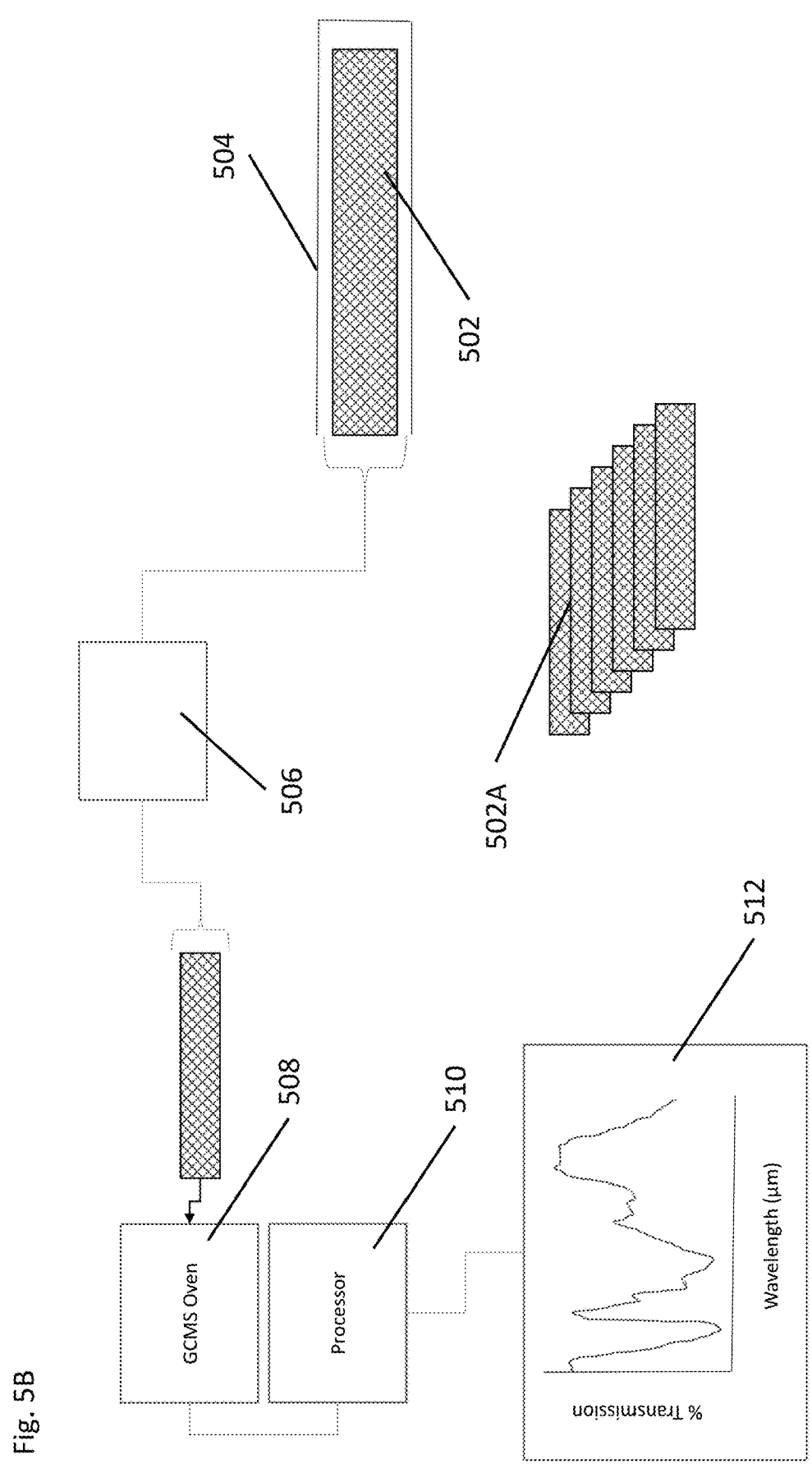
FIG. 5B illustrates a schematic view of a material analysis system in accordance with embodiments of the invention.

FIG. 5B illustrates a process similar to that illustrated in FIG. 4B with respect to the removal and analysis of the sample material. In many embodiments the sample material may be contained within a getter material 502 that is located within the cutting tool 504. Many embodiments may have a transfer device 506 for the mechanical removal of the getter material 502. In some embodiments the transfer device 506 may be connected directly to the cutting tool 504, while in other embodiments, the transfer device 506 may be located separately from the cutting tool 504. In accordance, with many embodiments, the transfer device 506 may mechanically remove the getter material 502 from the cutting tool 504 and deliver it to a Gas Chromatography Mass Spectrometer (GCMS) oven 508. In many embodiments, the GCMS oven 508 may be connected to a GCMS processor 510. The GCMS processor 510 may be configured to process and analyze the material data from the getter material 502. Accordingly, as one set of getter material 502 is being processed, the transfer device may select an additional getter material 502A to be inserted back into the cutting tool 504 for continuous processing. In some embodiments the system may have more than one transfer device to operate in conjunction with other transfer devices for removing and inserting getter materials (502 and 502A). In many embodiments, the analysis of the getter materials (502 and 502A) may be received by an output device 512 for displaying the results of the analysis. The output device, according to some embodiments, may be remotely located from the cutting tool 504.

Other embodiments of a cutting tool with porous regions may include an embedded or incorporated mechanical element that is positioned in the inner chamber of the tool and functions to physically move the permeated sample material along the inner chamber to an open end or extraction point on the cutting tool. From there, many embodiments, may incorporate a feed line connected to the extraction point where the sample can be transmitted directly to a GCMS oven or other type of analysis device. In accordance with some embodiments, the incorporated mechanical device may be a screw like feature such as an Archimedes screw or an impeller connected to a secondary motor to turn the screw thereby moving the sample material towards the extraction point. In some embodiments, the screw may be configured to rotate in conjunction with the rotation of the cutting tool to subsequently move the sample material towards the extraction point.

Figure 6:
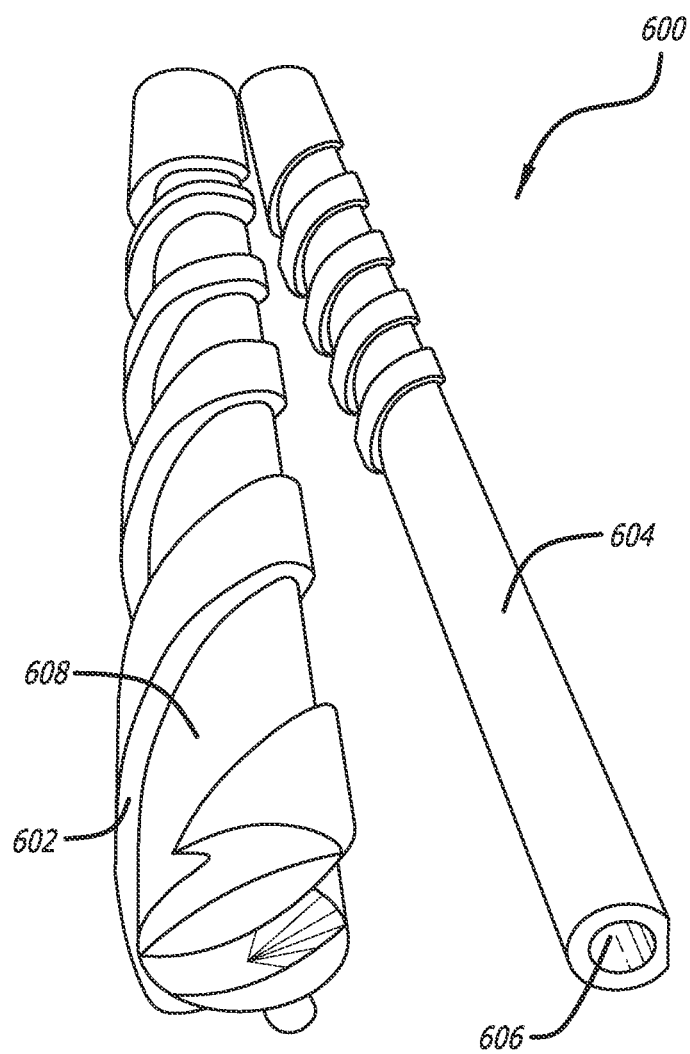
FIG. 6 illustrates end views of a drill bit in accordance with embodiments of the invention.

Although, FIGS. 1-5B illustrate embodiments of a cutting tool that resemble a traditional drill bit as well as processes by which material may be analyzed, it should be understood that the porous regions, the internal chamber and open ends or extraction points, as well as the material analysis could be implemented in an number of methods and/or cutting tools. FIGS. 6-8 illustrate other embodiments of cutting tools. FIG. 6 illustrates a cutting tool 600 in the shape of a traditional drill bit with a cutting portion 602 and a shaft portion 604 that has an open end 606. In many embodiments, the cutting portion 602 may have a plurality of porous elements 608 in a grid like pattern positioned between the cutting surfaces 602 of the tool 600. Similar to embodiments described in FIGS. 1-5B, embodiments similar to that shown in FIG. 6 can implement in-situ analysis tools and/or elements to perform in-situ analysis of captured sample material.

FIG. 7 illustrates an embodiment of a cutting tool 700 in the shape of a blade type tool. In some embodiments the cutting portion may be in the form of one or more blades 02 the extend in a plane outward from a shaft 04. The shaft 04 may be connected to an external motor or rotational device that can rotate the tool to cut the desired material. Additionally, many embodiments may have an internal chamber 06 that may be centrally located and may be in communication with other internal chambers that correspond to each of the plurality of blade elements 02. In many embodiments the blades may be made of a porous material as well as a combination of porous and non-porous material such that as the blade cuts through the material to be sampled it can simultaneously capture material samples through the permeation of the porous material. In accordance with some embodiments, the cutting tool 700 may have an additional extraction point 708 designed to aid in the removal of the sample material from the internal chamber. In accordance with some embodiments, the extraction points, either in the shaft or in an alternate location, can also be used to insert a material such as a fluid or lubricant to help with the drilling/cutting process.

Figure 7A:
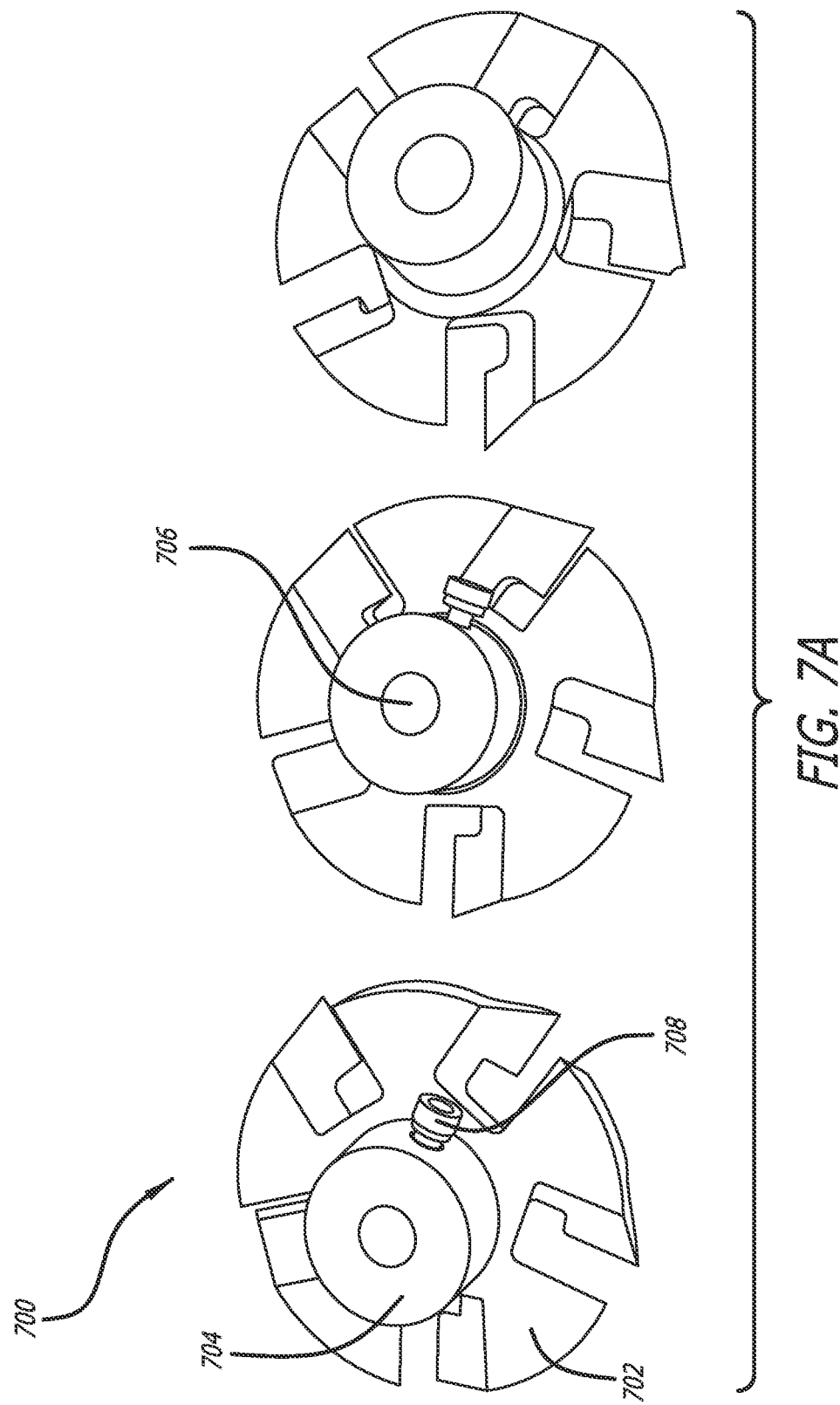
FIGS. 7A and 7B illustrate various saw blade type cutting tools in accordance with embodiments of the invention.
Figure 7B:
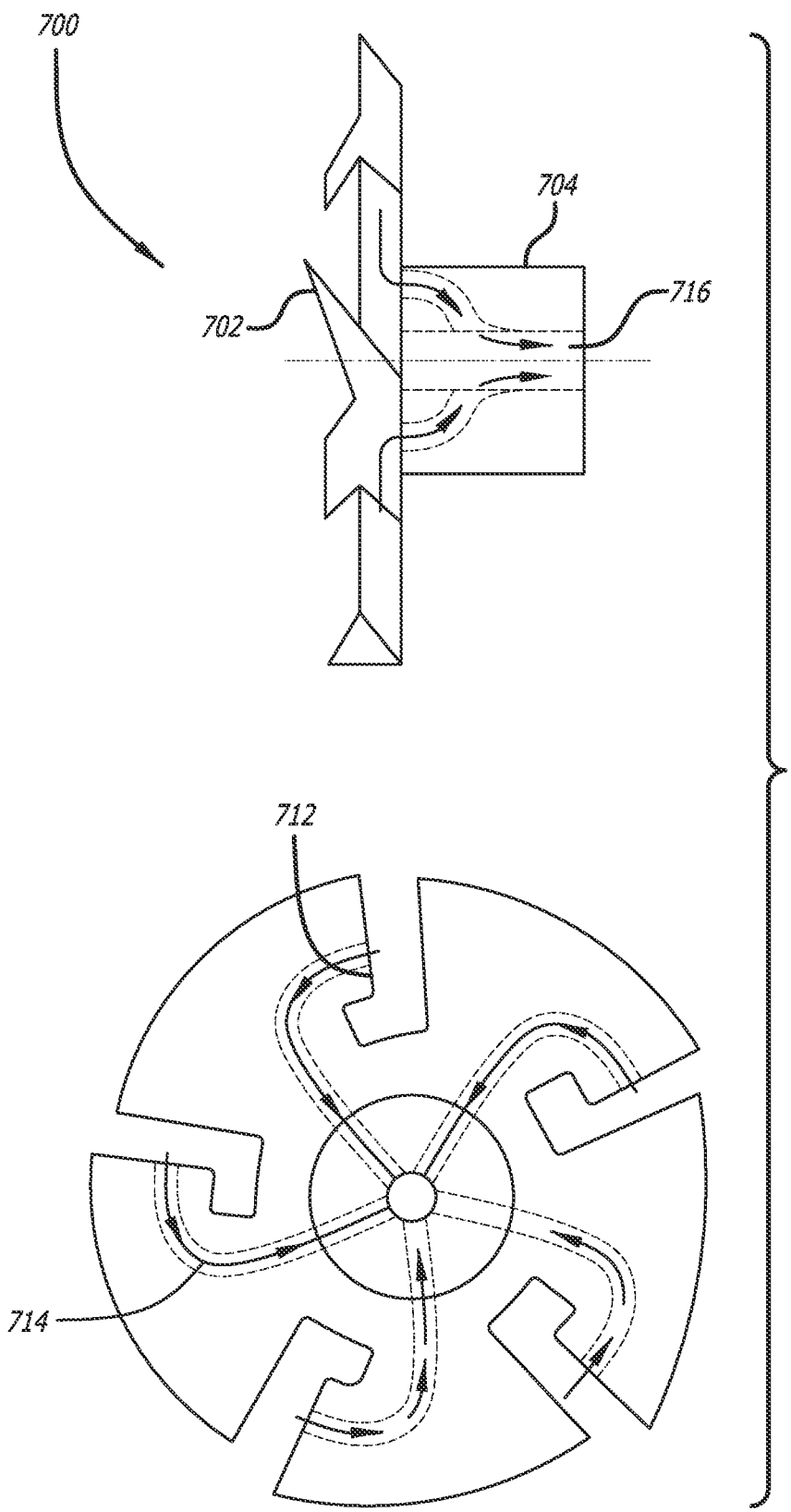

In accordance with other embodiments, the cutting tool may be configured to coring or boring through a sample material. For example, FIGS. 7A and 7B illustrate an embodiment of a coring tool 700 with multiple cutting surfaces 702. The coring tool 700, similar to other embodiments, may have a cutting surface 702 and a solid support surface 704. Additionally, FIG. 7B illustrates an embodiment that may incorporate a porous region 712 that may make up a portion of the support structure or cutting surface. In accordance with many embodiments, the porous regions 712 may have connecting chambers 714 that run from a portion of the porous regions to a central internal chamber 716. In many embodiments, the material can be directed through the connecting chambers to the central internal chamber and subsequently analyzed for content and composition.

Figure 8A:
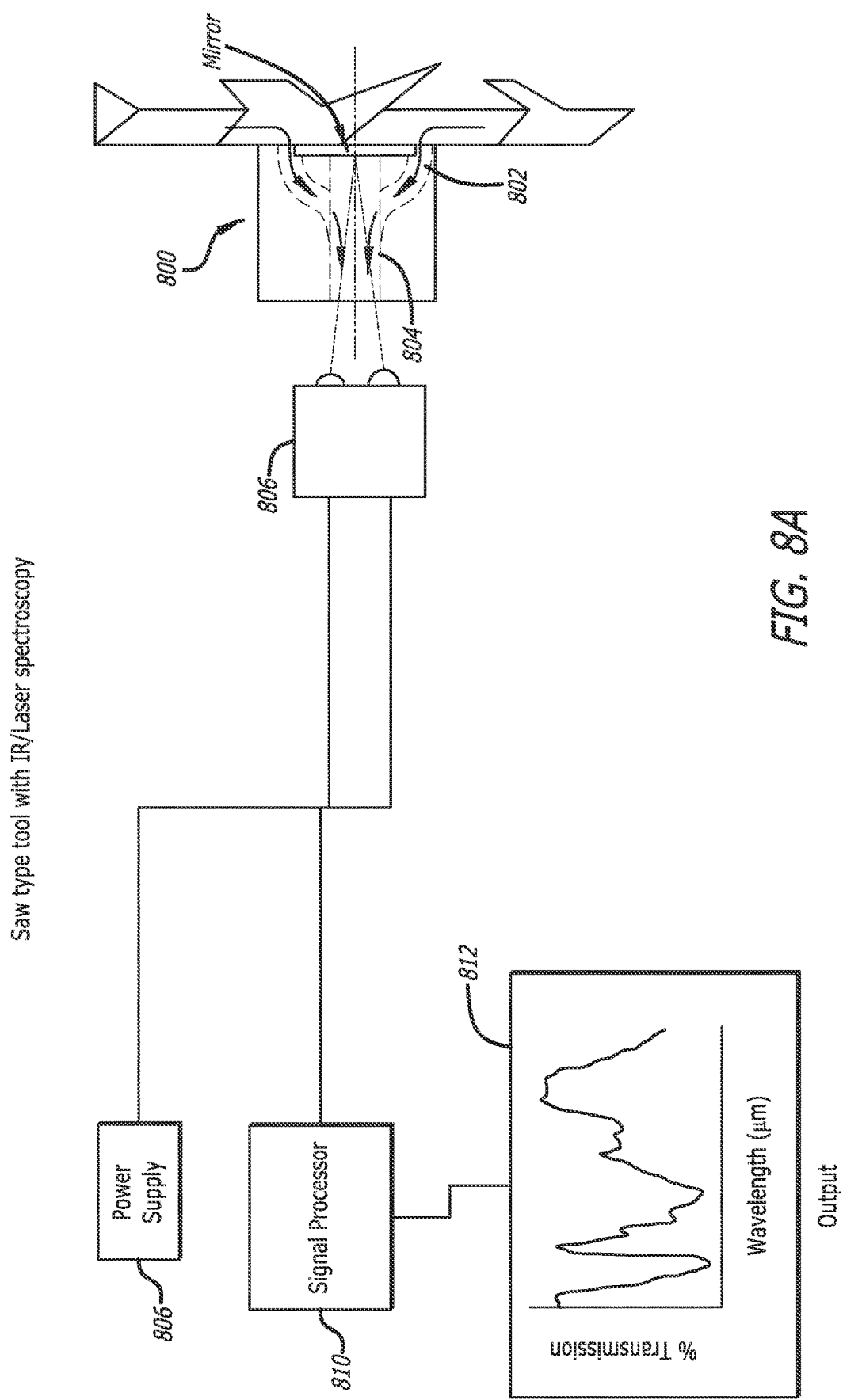
FIGS. 8A and 8B illustrate schematic views of material analysis systems in accordance with embodiments of the invention.
Figure 8B:
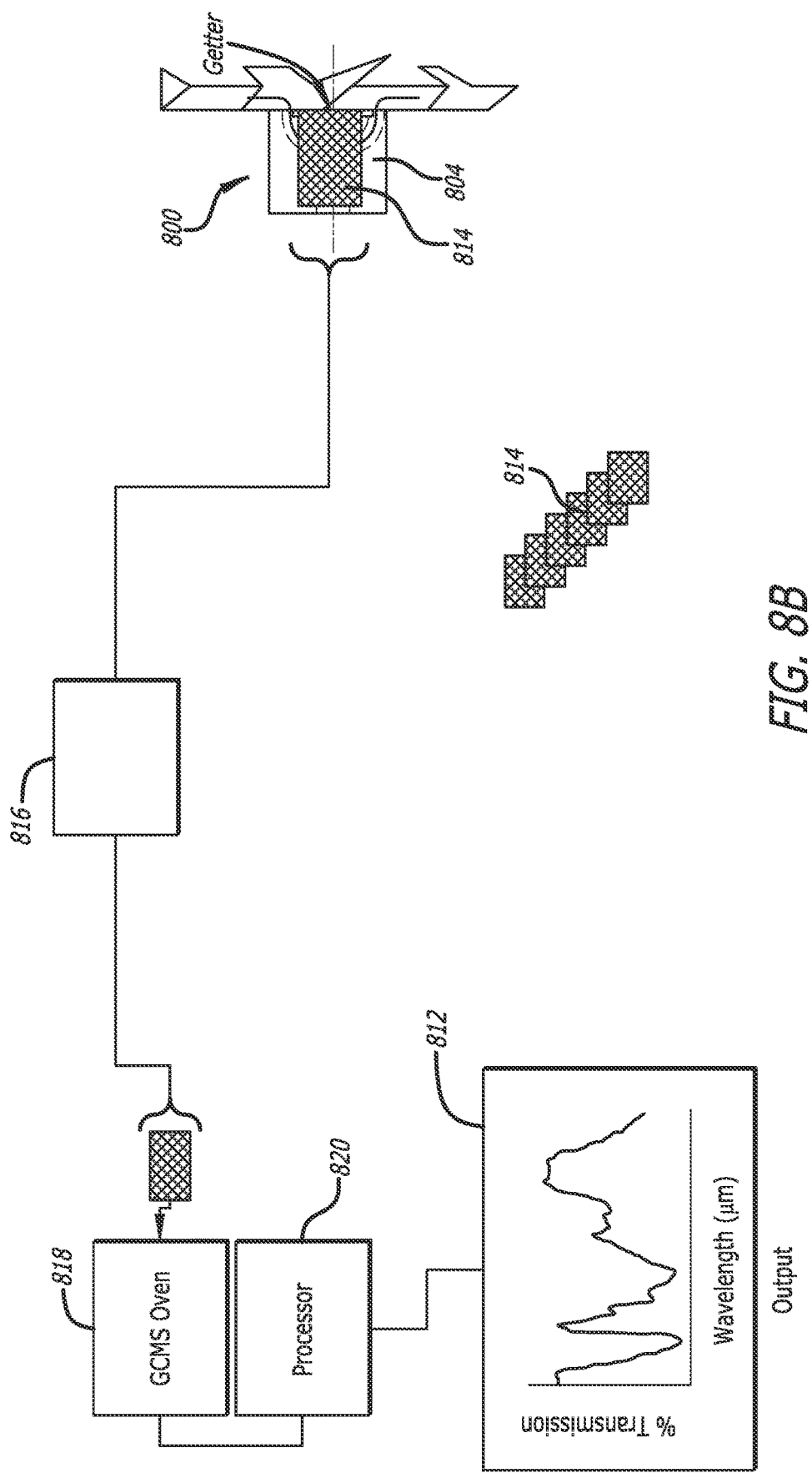

As with many other embodiments, cutting tools designed to core or bore through a material, such as those illustrated in FIGS. 7A and 7B, may be configured with additional material analysis components similar to those illustrated in FIGS. 4 and 5B. For example, FIGS. 8A and 8B illustrate embodiments of a coring type tool 800 with connecting chambers 802 connected to a central internal chamber 804 that are configured with in-situ analysis components. For example, FIG. 8A illustrates a cutting tool 800 connected to an imaging device 806 where the imaging device may be configured to send and receive a signal to and from the central internal chamber 804 such that the signal would interact with the material. In many embodiments, the signal may be a light. In some embodiments, the signal may be an IR signal. In many embodiments, the imaging device may be powered by a power supply 808 that may be integrated with the imaging device 806 or may be separate. The imaging device, in accordance with many embodiments, can direct any received signals to a signal processor unit 810 that can be used to analyze the data on the material. Subsequently, many embodiments may include an output module 812 for interpreting the data results. Similarly, FIG. 8B illustrates a process by which a cutting tool 800 may be configured with a getter material 814 that is placed inside the central internal chamber 804. Once the getter material 814 has interacted with the received sample material it can be removed by a transfer tool 816 and then placed in a GCMS oven 818 for processing. The oven 818 may be connected to a data processor 820 that can process the data and subsequently transmit the processed data to an output device 812 for interpretation. In accordance with many embodiments, the data processor 820 may be a GCMS data processor.

Figure 9:
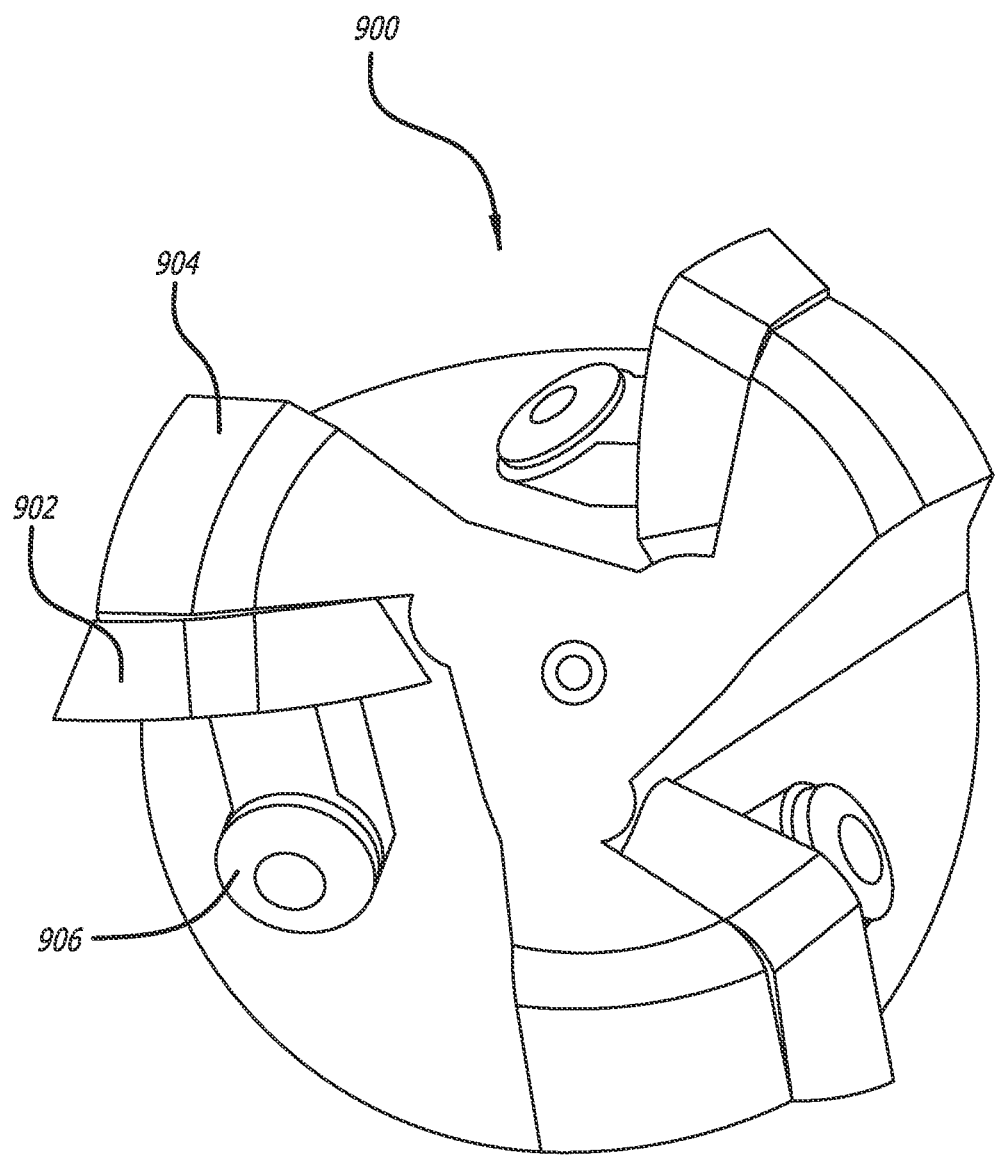
FIG. 9 illustrates a cutting tool in accordance with embodiments of the invention.
Figure 10:
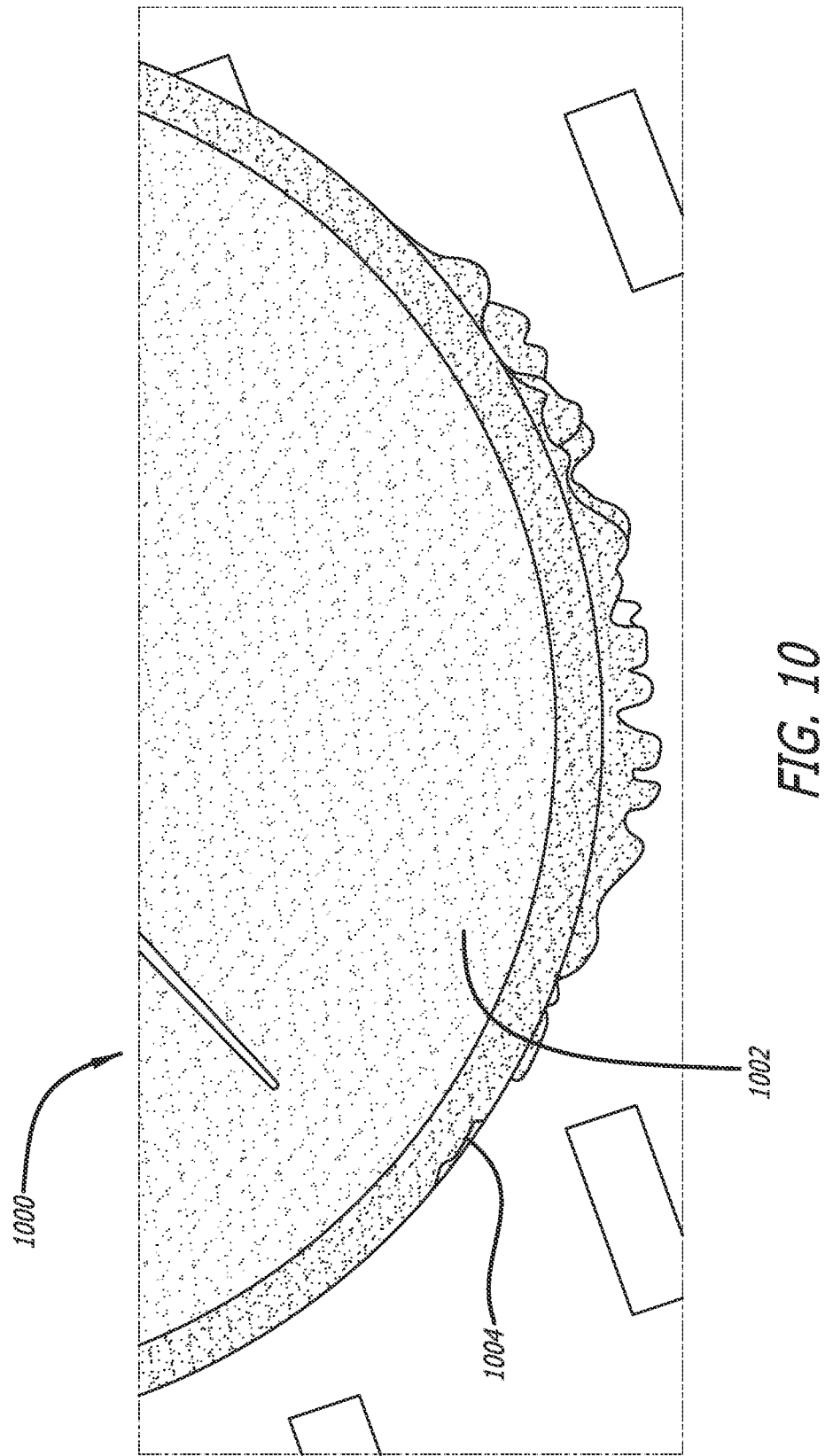
FIG. 10 illustrates a metallic blade element with a porous and solid region in accordance with embodiments of the invention.

Turning now to FIGS. 9 and 10, other embodiments of cutting tools are illustrated. For example, FIG. 9 illustrates a coring tool 900 similar to those seen in FIGS. 7A through 8B. However, some embodiments may incorporate a cutting element 902 that is attached to a support element of the tool 904 by a mounting point 706. In some embodiments, the cutting element 902 may have an integrated porous region (not shown). In other embodiments, the porous region may be integrated with a portion of the support elements 904 of the tool. FIG. 10 illustrates an embodiment of a cutting tool 1000 with a centralized porous region 1002 connected to a more solid external region 1004. In many embodiments, the external region 1004 may contain internal chambers (not shown) that can carry sample material away to be analyzed. In many embodiments the internal chambers may be connected to the porous region 1002.

The complexities of the various embodiments described herein may implement one or more different materials and/or manufacturing methods to achieve the desired product with the desired capabilities. For example, many embodiments may incorporate one or more materials in the fabrication of the tools. Some embodiments, may use tungsten-carbide. Other embodiments may use a combination of materials such as iron, nickel, titanium, zirconium, or any number of alloys such as maraging steel, carbon steel, stainless steel, tool steel, precipitation hardened steel, Inconel, Ti-6Al-4V, bulk metallic glass, nickel superalloy, shape memory alloys, Nitinol, and/or high entropy alloys.

Likewise, many embodiments may use a custom combination of materials and/or geometries in the overall design of the tool to create a tool that is optimized for efficient removal and sampling. For example, some tools may adjust the length of the internal chambers, previously discussed, to create an optical channel that is tuned to the wavelength of the analysis instruments. Additionally, the tool's composition and design can be optimized for the desired cutting process and subsequent sampling. Some embodiments may incorporate a tool designed to be submerged in water, oil, or gas and subsequently sample such elements. Additionally, some embodiments may be designed to cut through ice, rock, or another hard substance and be configured to capture liquids, and gases trapped in the hard substance. Such tools can be optimized with material and geometry to perform according to the sampling technique and cutting desired. Many embodiments are configured to capture material samples and perform in-situ analysis through the porous regions of the tool, however, some embodiments may utilize the porous regions an internal shaft to move fluid or gases from the tool to the material being cut. Accordingly, such embodiments can help to prevent tool wear as well as provide for additional sensing capabilities of the tool during cutting. For example, some embodiments may implement pressure transducers to measure forces on the tool to help determine the relative composition of the material being cut. Accordingly, movement of the cutting tool can be adjusted. Additionally, as illustrated above, many embodiments can perform in-situ analysis of the material that can likewise be used to adjust the movement of the tool in the material. As can be appreciated, the various methods in which embodiments of cutting tools with porous regions can implemented can make them ideal for a variety of industries including mining, such as oil and gas, as well as fracking, and space based material sampling and or mining.

In addition to the varieties of materials that can be used in the many embodiments, alternative manufacturing methods can be used to produce the complex structured described. For example, many embodiments may utilize additive manufacturing to produce the various embodiments. Additive manufacturing can allow for complex structures to be produced without the need for multiple iterations of tooling that can be costly. Moreover, the combination of one or more materials used in the various embodiments makes additive manufacturing a good candidate for production methods that can save cost and time. In accordance with many embodiments, the cutting tools described herein may be produced by any number of additive manufacturing methods depending on the material used and the overall design. Such embodiments may include powder bed fusion, directed energy deposition, ultrasonic additive manufacturing, binder jetting, material jetting, cold spraying, friction welding, and/or material extrusion. In accordance with many embodiments, the additive manufacturing process may involve the sintering or partial sintering of the metallic materials in order to produce the combination of solid and porous regions of embodiments of cutting tools. Additionally, some embodiments may incorporate laser sintering to create the different areas of the cutting tool. In accordance with some embodiments, the cutting tools may be produced by a combination of manufacturing methods such as additive manufacturing and traditional machining and/or material deposition. Many embodiments may also include the addition of coatings and or other components to create the final cutting tool.

In various embodiments, the additive manufacturing process can be used to directly control the forming process of the materials to form the porous regions in the various embodiments of cutting tools. As described previously, many embodiments may utilize a number of materials and/or metals to manufacture embodiments of the cutting tools. In some embodiments the additive manufacturing is directly controlled to enable the use of materials in their native alloy condition such that additional resins and/or bonding agents do not have to be used to generate the porous regions of the cutting tools. For example, many embodiments incorporate design characteristics such that the porous regions of a cutting tool can be built into the tool as it is manufactured without the use of resins that might be burned off during sintering to leave behind holes or pores in the tool. Moreover, many embodiments enable the manufacture of the cutting portion, support portion, and porous portion within the cutting tool simultaneously.

Doctrine of Equivalents

As can be inferred from the above discussion, the above-mentioned concepts can be implemented in a variety of arrangements in accordance with embodiments of the invention. Specifically, many embodiments are directed to a cutting tool with a porous region that is capable of accepting sample materials for in-situ analysis. Achieving such functionality, according to embodiments, involves the implementation of special arrangements/designs between subsystems described above, and their equivalents.

Accordingly, although the present invention has been described in certain specific aspects, many additional modifications and variations would be apparent to those skilled in the art. It is therefore to be understood that the present invention may be practiced otherwise than specifically described. Thus, embodiments of the present invention should be considered in all respects as illustrative and not restrictive.

What is claimed is:

1. A cutting tool comprising:
   a support region that cooperatively engages with a rotational motor;
   a cutting region with a cutting element and connected to the support region such that a rotation induced from the rotational motor would equate to a corresponding rotation of the cutting region;
   an internal chamber disposed within the cutting tool, wherein the internal chamber connects both the cutting region and the supporting region and wherein the internal chamber has an opening in at least the support region; and
   a porous region disposed in at least a portion of the cutting or the support region wherein the porous region comprises a plurality of porous elements disposed between a plurality of support elements that interconnect the porous region with the cutting region and the support region, and wherein the porous region receives a sample material through the porous elements and directs the sample material into the internal chamber such that the sample material can be analyzed.

2. The cutting tool of claim 1, further comprising an in-situ testing component wherein the testing component comprises
   a light source disposed at the opening of the internal chamber and wherein the light source is configured to project light within the internal chamber towards a reflective element disposed within the internal chamber of the cutting tool; and
   a detector disposed at the opening of the internal chamber wherein the detector receives a reflected signal from the reflective element.

3. The cutting tool of claim 2, wherein the in-situ testing component is electronically connected to a data analysis element configured to analyze a set of data produced by the detector.

4. The cutting tool of claim 1, wherein the porous region is made from a material selected from the group consisting of maraging steel, carbon steel, stainless steel, tool steel, precipitation hardened steel, Inconel, Ti-6Al-4V, bulk metallic glass, nickel superalloy, shape memory alloys, Nitinol, and high entropy alloys.

5. The cutting tool of claim 1, wherein the porous region is made of a partially sintered metallic component such that the plurality of porous elements allow gas or liquid to permeate through the porous region.

6. The cutting tool of claim 1, wherein the internal chamber has a getter material disposed therein such that the getter material is exposed to and interacts with the sample material received through the plurality of porous elements.

7. The cutting tool of claim 1, further comprising a mechanical device disposed within the internal chamber such that the mechanical device can interact with the sample material and move the sample material within the internal chamber.

8. The cutting tool of claim 7, wherein the mechanical device is selected from a group consisting of an impeller and a screw.

9. The cutting tool of claim 1, wherein the cutting portion of the tool contains tungsten-carbide.

10. The cutting tool of claim 1, wherein the cutting tool is made from a material selected from the group consisting of iron, nickel, titanium, and zirconium.

11. The cutting tool of claim 1, wherein the internal chamber is configured to receive a fluid material through the opening and wherein the fluid material is pushed through the porous region to the external environment or material being cut.

12. The cutting tool of claim 1, wherein the support region, the cutting region, and the porous region have the same material composition.

13. The cutting tool of claim 1, wherein the support region, the cutting region, and the porous region have different material compositions.

14. The cutting tool of claim 1, wherein the plurality of porous elements range in size from 100 nm to 1 mm.

15. The cutting tool of claim 1, having an extraction hole that is disposed within the support region and interconnects with the internal chamber, wherein the extraction hole is connected to an external analysis device that receives at least a portion of the sample material from within the internal chamber for analysis.

16. The cutting tool of claim 1, wherein the analysis is done by spectrometry.

17. The cutting tool of claim 1, having a plurality of cutting regions wherein each of the plurality of cutting regions is each connected to the support element and wherein each of the plurality of cutting regions has a correlating internal chamber that interconnects to an internal chamber of the support region.

18. The cutting tool of claim 17, wherein the porous region is disposed in at least a portion of each of the plurality of cutting regions.

19. The cutting tool of claim 1, wherein the tool is manufactured using an additive manufacturing process.

20. The cutting tool of claim 19, wherein the additive manufacturing process is selected from a group consisting of powder bed fusion, directed energy deposition, ultrasonic additive manufacturing, binder jetting, material jetting, cold spraying, friction welding, and material extrusion.

21. A method for material extraction and analysis comprising:
   Obtaining a material cutting tool wherein the cutting tool comprises;
       a support region that cooperatively engages with a rotational motor;

a cutting region with a cutting element and connected to the support region such that a rotation induced from the rotational motor would equate to a corresponding rotation of the cutting region;

an internal chamber disposed within the cutting tool, wherein the internal chamber connects both the cutting region and the supporting region and wherein the internal chamber has an opening in at least the support region; and a porous region disposed in at least a portion of the cutting or the support region wherein the porous region comprises a plurality of porous elements disposed between a plurality of support elements that interconnect the porous region with the cutting region and the support region;

receiving a sample material through the porous elements;

directing the sample material into the internal chamber;

projecting a signal from an imaging device towards the internal chamber wherein the signal can interact with the sample material and produce a reflective signal wherein the reflective signal is received by a signal detector; and processing the reflective signal to determine the material type and composition.

\* \* \* \* \*